US008889849B2

(12) United States Patent
Delaney, IV et al.

(10) Patent No.: US 8,889,849 B2
(45) Date of Patent: Nov. 18, 2014

(54) HCV GENOTYPE 4 REPLICONS

(75) Inventors: William E. Delaney, IV, Foster City, CA (US); Guofeng Cheng, Foster City, CA (US); Hongmei Mo, Palo Alto, CA (US); Simin Xu, Palo Alto, CA (US); Betty Peng, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 33 days.

(21) Appl. No.: 13/542,554

(22) Filed: Jul. 5, 2012

(65) Prior Publication Data
US 2013/0052634 A1    Feb. 28, 2013

Related U.S. Application Data

(60) Provisional application No. 61/504,853, filed on Jul. 6, 2011, provisional application No. 61/509,984, filed on Jul. 20, 2011, provisional application No. 61/589,789, filed on Jan. 23, 2012.

(51) Int. Cl.
*C12Q 1/70* (2006.01)
*C12Q 1/66* (2006.01)
*C12N 15/86* (2006.01)
*C12N 5/10* (2006.01)
*C12N 5/071* (2010.01)
*C07K 14/005* (2006.01)
*G01N 33/576* (2006.01)
*C12Q 1/68* (2006.01)
*C12N 15/64* (2006.01)
*C12N 15/65* (2006.01)

(52) U.S. Cl.
CPC .............. *C12N 15/86* (2013.01); *C07K 14/005* (2013.01); *C12N 2770/24231* (2013.01); *G01N 33/5767* (2013.01); *C12N 2770/24222* (2013.01); *G01N 2333/186* (2013.01); *C12N 2770/24243* (2013.01)
USPC .......... 536/23.72; 435/5; 435/370; 435/320.1

(58) Field of Classification Search
CPC ........ C12N 15/64; C12N 15/65; C12N 15/86; C12N 2015/79; C12N 2770/24222; C12N 2770/24231; C12N 2770/24243; C12Q 1/70; C12Q 1/707
See application file for complete search history.

(56) References Cited

FOREIGN PATENT DOCUMENTS

| WO | WO-2004/039970 | 5/2004 |
| WO | WO-2005/053516 | 6/2005 |
| WO | WO-2009/071488 | 6/2009 |
| WO | WO-2011/038737 | 4/2011 |

OTHER PUBLICATIONS

Kamal et al. Hepatitis C Genotype 4: What we know and what we don't yet know. Hepatology 2008, vol. 47, pp. 1371-1383.*
Peng et al. Development of Robus Hepatitis C Virus Genotype 4 Subgenomic Replicons. Gastroenterology 2013, vol. 144, pp. 59-61.*
Gottwein et al. Novel infectious cDNA clones of hepatitis C virus genotype 3a (strain S52) and 4a (strain ED43). Journal of Virology 2010, vol. 84, No. 10, p. 5277-5293.*
Scheel et al. Development of JFH1-based cell culture systems for hepatitis C virus genotype 4a and evidence for cross-genotype neutralization. Proceedings from the National Academy of Sciences of the USA 2008, vol. 105, No. 3, p. 997-1002.*
U.S. Appl. No 13/542,551, filed Jul. 5, 2012, Delaney, IV.
Author unknown, "Hepatitis C virus partial NS3 protease", retrieved from EBI <http://www.ebi.ac.uk/ena/data/view/ABD65842&display=text>, database accession No. ABD65842 sequence, 2006.
Blight et al., "HCV Replicon Systems", Source Hepatitis C Viruses: Genomes and Molecular Biology, 2006, pp. 311-351.
International Search Report and Written Opinion for PCT/US2012/045592 dated Nov. 15, 2012.
International Search Report and Written Opinion for PCT/US2012/045593 dated Dec. 3, 2012.
Khaliq et al., "Down-regulation of IRES containing 5'UTR of HCV genotype 3a using siRNAs", Virology Journal, vol. 8, No. 1, 2011, pp. 223-224.
O'Boyle et al., "Development of a Cell-based High-throughput Specificity Screen Using a Hepatitis C Virus—Bovine Viral Diarrhea Virus Dual Replicon Assay", Antimicrobial Agents and Chemotherapy, vol. 49, No. 4, 2005, pp. 1346-1353.
Peng et al., "825 Development and Molecular Characterization of a Robust Genotype 4 Hepatitis C Virus Subgenomic Replicon", Journal of Hepatology, vol. 56, 2012, 1 page.
Winters et al., "Hepatitis C virus protease gene diversity in patients coinfected with human immunodeficiency virus", Journal of Virology, vol. 80, No. 8, 2006, pp. 4196-4199.
Zekri et al., "Consensus siRNA for Inhibition of HCV genotype-4 replication", Virology Journal, London, vol. 6, No. 1, 2009, 9 pgs.
Gottwein et al. Robust hepatitis C genotype 3a cell culture releasing adapted intergenotypic 3a/2a (S52/JFH1) viruses. Gastroenterology 2007, vol. 133, p. 1614-1626.
Kuiken et al. Nomenclature and numbering of the hepatitis C virus, Methods Mol Biol. 2009;510:33-53.

* cited by examiner

*Primary Examiner* — Louise Humphrey
(74) *Attorney, Agent, or Firm* — Sheppard Mullin Richter & Hampton LLP

(57) ABSTRACT

Replicons of genotype 4 hepatitis C virus (HCV) are provided. These replicons contains adaptive mutations giving rise to the HCV's capability to replicate in vitro. Methods of preparing genotype 4 replicons and methods of using these replicons to screen antiviral agents are also provided.

20 Claims, 4 Drawing Sheets

HCV GENOTYPE 4 REPLICONS

CROSS REFERENCE TO RELATED APPLICATIONS

This application claims the benefit under 35 U.S.C. §119(e) of U.S. Provisional Applications Ser. No. 61/504,853 filed Jul. 6, 2011, Ser. No. 61/509,984 filed Jul. 20, 2011, and Ser. No. 61/589,789 filed Jan. 23, 2012, the content of each of which is incorporated by reference in its entirety into the present disclosure.

SEQUENCE LISING

The instant application contains a Sequence Listing which has been submitted electronically in ASCII format and is hereby incorporated by reference in its entirety. Said ASCII copy, created on May 28, 2014, is named 37JD192881$_{13}$SL.txt and is 41,281 bytes in size.

FIELD OF THE DISCLOSURE

The disclosure is directed to hepatitis C replicons of genotype 4 and methods of preparing and using the replicons.

SEQUENCE LISTING

The instant application contains a Sequence Listing which has been submitted in ASCII format via EFS-Web and is hereby incorporated by reference in its entirety. Said ASCII copy, created on Oct. 24, 2012, is names 457103202.txt and is 2,182 bytes in size.

STATE OF THE ART

Chronic hepatitis C virus (HCV) infection remains a significant global heath burden with an estimated 160 million people infected world wide. The current standard of care is 24 to 48 week courses of pegylated interferon plus ribavirin. Due to the partial efficacy and poor tolerability of this regimen, the discovery and development of new antiviral agents has been intensely pursued. Recently, these efforts have culminated in the FDA approval of two NS3 protease inhibitors (boceprevir and telaprevir) for use in combination with pegylated interferon and ribavirin for the treatment of chronic genotype 1 HCV infection. Many other inhibitors are in advanced clinical development, however, the majority are being developed to treat genotype 1 infections.

HCV is a positive-strand RNA virus that exhibits extraordinary genetic diversity. Six major genotypes (i.e. genotype 1-6) along with multiple subtypes (e.g. genotype 1a, 1b, 1c etc.) have been reported. Genotypes 1, 2 and 3 have worldwide distributions. Genotypes 1a or 1b are generally predominant in North America, South America, Europe and Asia. However, genotypes 2 and 3 are common and can constitute 20 to 50% of infections in many of these areas. Genotype 4a is the predominant in the Middle East and many African countries; up to 15% of the population of Egypt is infected with HCV and 93% of infections are genotype 4. Genotype 5 is prevalent in South Africa, while Genotype 6 is most common in Asia. Although most continents and countries have a "dominant" genotype, infected populations are almost universally made up of a mixture of multiple genotypes. Furthermore, the geographical distribution and diversity (epidemiology) of HCV infection is continuously evolving, due to large-scale immigration and widespread intravenous drug use. For instance, genotype 4a has noticeably spread into central and northern Europe. This presents a clinical challenge, since it is well documented that individual genotypes respond differently to both direct antivirals and immunomodulatory therapies, including the current standard of care.

HCV replicons are self-replicating RNA sequences derived from the HCV genome and have served as workhorses both for molecular virology studies and drug discovery. To date, replicons have been established from two genotypes and three subtypes (genotypes 1a, 1b and 2a). These replicons have been crucial in multiple aspects of drug discovery and development including the identification of novel inhibitor classes, the optimization of clinical candidates and the characterization of clinical resistance. Recently, there has been increasing interest in developing next-generation drugs that are active against all major HCV genotypes. Ideally, the approval of "pan-genotypic" drugs and regimens will greatly simplify the treatment of HCV.

A key step in the pursuit of pan-genotypic treatment regimens will be the development of in vitro tools that allow the study of all major genotypes and subtypes. Replicons derived from sequences of additional major genotypes (i.e. those other than genotype 1a, 1b or 2a), however, have not been generated. In particular, despite the worldwide prevalence of genotype 4 HCV in the Middle East, North Africa and Europe, no genotype 4 replicons have been described.

SUMMARY

It has been discovered, unexpectedly, that clonal cell lines stably replicating Genotype 4 replicons were obtained by transcribing and electroporating subgenomic genotype 4 cDNAs into HCV permissive cell lines. Adaptive mutations have been identified from these clones, as compared to the wildtype virus. When these mutations were engineered by site-directed mutagenesis and introduced into the cell lines, HCV genotype 4 replications ensued.

These adaptive mutations for genotype 4 were located in NS3 (T343K/R, A200E, or T511R), NS4A (Q34K/R, or E52V) or NS5A (L179P). The establishment of robust genotype 4 replicon systems provides powerful tools to facilitate drug discovery and development efforts.

Accordingly, one embodiment of the present disclosure provides a genotype 4 hepatitis C viral (HCV) RNA construct that is capable of replication in a eukaryotic cell, wherein the RNA sequence comprises a 5'NTR, an internal ribosome entry site (IRES), sequences encoding one or more of NS3, NS4A, NS4B, NS5A or NS5B, and a 3'NTR.

In one aspect, the construct comprises one or more adaptive mutations in NS3, NS4A, NS4B, NS5A or NS5B. Non-limiting examples include (1) an isoleucine at location 2204 (residue 232 of NS5A, (2) a glutamic acid at residue 200, a lysine or an arginine at residue 343, an arginine at residue 511, or combinations thereof in NS3, (3) a lysine or an arginine at residue 34, a valine at residue 52, or combinations thereof in NS4A, or (4) a proline at residue 179 in NS5A. It is also contemplated that the construct includes at least two, or alternatively three or four adaptive mutations. In one aspect, the adaptive mutations come from different genes. In some aspects, the construct is a subgenomic or full-length HCV replicon.

Moreover, DNA that transcribes to the RNA construct, viral particles that include the RNA construct, and cells containing such DNA or RNA are also provided.

Also provided, in one embodiment, are individual NS3, NS4A or NS5A proteins that include one or more of the corresponding adaptive mutations. Polynucleotides encoding these proteins and antibodies that specifically recognize the proteins are also provided.

In another embodiment, the present disclosure provides an isolated cell comprising a genotype 4 hepatitis C viral (HCV) RNA that replicates in the cell. In one aspect, there is an absence, in the cell, of a DNA construct encoding the RNA. In another aspect, the cell comprises at least 10 copies, or alternatively at least about 100, 500, 1000, 2000, 5000, 10,000, $1 \times 10^5$, $1 \times 10^6$, $1 \times 10^7$, $1 \times 10^8$ or $1 \times 10^9$ copies of the RNA. In any of such aspects, the RNA can be a subgenomic HCV sequence or a full-length HCV sequence and can include one or more of the adaptive mutations described above.

In one aspect, the cell is a mammalian cell which can be, for instance, a hepatoma cell, in particular a Huh7 1C cell.

Methods of improving the capability of a genotype 4 HCV viral RNA to replicate in a eukaryotic cell are also provided, comprising one or more of (a) substituting residue 200 of NS3 with a glutamic acid, (b) substituting residue 343 of NS3 with a lysine or an arginine, (c) substituting residue 511 of NS3, with an arginine, (d) substituting residue 34 of NS4A with a lysine or an arginine, (e) substituting residue 52 of NS4A with a valine, or (f) substituting residue 179 of NS5A with a proline.

Still provided, in one embodiment, is a method of identifying an agent that inhibits the replication or activity of a genotype 4 HCV, comprising contacting a cell of any of the above embodiments with a candidate agent, wherein a decrease of replication or a decrease of the activity of a protein encoded by the RNA indicates that the agent inhibits the replication or activity of the HCV. Alternatively, the method comprises contacting the lysate of a cell of any of the above embodiments with a candidate agent, wherein a decrease of the activity of a protein encoded by the RNA indicates that the agent inhibits the activity of the HCV.

BRIEF DESCRIPTION OF THE DRAWINGS

The disclosure is best understood from the following detailed description when read in conjunction with the accompanying drawings. Included in the drawings are the following figures.

DETAILED DESCRIPTION

Figure 1:
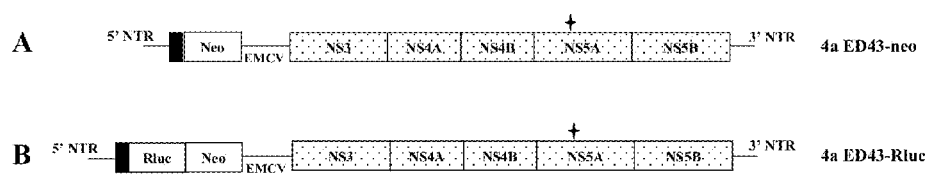
FIG. 1 is a schematic diagram of genotype 4a replicon constructs. HCV replicons used to generate novel genotype 4a stable replicon cell lines. ED43 4a strain replicons encode either a nenomycin phosphotransferase II (A) or a Renilla luciferase (Rluc)-neomycin phosphotransferase II fusion reporter (B). The synthesized replicons incorporated the following elements from 5' to 3': the ED43 5'UTR; the neomycin phosphotransferase II gene (neo) or Rluc-Neo gene; the encephalomyocarditis virus (EMCV) IRES; the NS3-NS5B polyprotein region of ED43 including an NS5A adaptive mutation (S2204I) and the 3'UTR of ED43. Solid black boxes indicate HCV core sequence. Dot shaded boxes indicate HCV polyprotein sequence. "+" indicates the S2204I adaptive mutation. The 5' and 3' non-translated regions (NTR), and EMCV IRES are indicated.

Prior to describing this disclosure in greater detail, the following terms will first be defined.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

It must be noted that as used herein and in the appended claims, the singular forms "a", "an", and "the" include plural referents unless the context clearly dictates otherwise. Thus, for example, reference to "a thread" includes a plurality of threads.

1. Definitions

Unless defined otherwise, all technical and scientific terms used herein have the same meaning as commonly understood by one of ordinary skill in the art to which this disclosure belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed disclosure. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. Single letter and three letter abbreviations of the naturally occurring amino acids are listed below. A peptide of three or more amino acids is commonly called an oligopeptide if the peptide chain is short. If the peptide chain is long, the peptide is commonly called a polypeptide or a protein.

| 1-Letter | 3-Letter | Amino Acid |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine |

The terms "polynucleotide" and "oligonucleotide" are used interchangeably and refer to a polymeric form of nucleotides of any length, either deoxyribonucleotides or ribonucleotides or analogs thereof Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention. In one embodiment, the homologous peptide is one that shares the same functional characteristics as those described, including one or more of the adaptive mutations.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: www.ncbi.nlm.nih.gov/blast/Blast.cgi, last accessed on Jul. 15, 2011. Biologically equivalent polynucleotides are those having the specified percent homology and encoding a polypeptide having the same or similar biological activity.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. A eukaryotic host, including, for example, yeast, higher plant, insect and mammalian cells, or alternatively from a prokaryotic cells as described above. Non-limiting examples include simian, bovine, porcine, murine, rats, avian, reptilian and human.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein. The antibodies can be polyclonal or monoclonal and can be isolated from any suitable biological source, e.g., murine, rat, sheep and canine.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "isolated" as used herein refers to molecules or biological or cellular materials being substantially free from other materials or when referring to proteins or polynucleotides, infers the breaking of covalent bonds to remove the protein or polynucleotide from its native environment. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. The term "isolated" is also used herein to refer to cells or tissues that are isolated from other cells or tissues and is meant to encompass both cultured and engineered cells or tissues.

Hepatitis C virus or "HCV" is a small (55-65 nm in size), enveloped, positive-sense single-stranded RNA virus of the family Flaviviridae. Hepatitis C virus is the cause of hepatitis C in humans. The hepatitis C virus particle consists of a core of genetic material (RNA), surrounded by an icosahedral protective shell of protein, and further encased in a lipid (fatty) envelope of cellular origin. Two viral envelope glycoproteins, E1 and E2, are embedded in the lipid envelope.

Hepatitis C virus has a positive sense single-stranded RNA genome. The genome consists of a single open reading frame that is 9600 nucleotide bases long. This single open reading frame is translated to produce a single protein product, which is then further processed to produce smaller active proteins.

At the 5' and 3' ends of the RNA are the UTR, that are not translated into proteins but are important to translation and replication of the viral RNA. The 5' UTR has a ribosome binding site (IRES—Internal ribosome entry site) that starts the translation of a very long protein containing about 3,000 amino acids. This large pre-protein is later cut by cellular and viral proteases into the 10 smaller proteins that allow viral replication within the host cell, or assemble into the mature viral particles.

Structural proteins made by the hepatitis C virus include Core protein, E1 and E2; nonstructural proteins include NS2, NS3, NS4, NS4A, NS4B, NS5, NS5A, and NS5B.

Based on genetic differences between HCV isolates, the hepatitis C virus species is classified into six genotypes (1-6) with several subtypes within each genotype (represented by letters). Subtypes are further broken down into quasispecies based on their genetic diversity. The preponderance and distribution of HCV genotypes varies globally. For example, in North America, genotype 1a predominates followed by 1b, 2a, 2b, and 3a. In Europe, genotype 1b is predominant followed by 2a, 2b, 2c, and 3a. Genotypes 4 and 5 are found almost exclusively in Africa. Genotype is clinically important in determining potential response to interferon-based therapy and the required duration of such therapy. Genotypes 1 and 4 are less responsive to interferon-based treatment than are the other genotypes (2, 3, 5 and 6). Duration of standard interferon-based therapy for genotypes 1 and 4 is 48 weeks, whereas treatment for genotypes 2 and 3 is completed in 24 weeks.

Sequences from different HCV genotypes can vary as much as 33% over the whole viral genome and the sequence variability is distributed equally throughout the viral genome, apart from the highly conserved 5' UTR and core regions and the hypervariable envelope (E) region.

HCV genotypes can be identified with various methods known in the art. PCR-based genotyping with genotype-specific primers was first introduced in 1992, in particular with primers targeting the core region. Commercial kits (e.g., InnoLipa® by Innogenetics (Zwijindre, Belgium)) are also available. Direct sequencing, in the vein, can be used for more reliable and sensitive genotyping.

Serologic genotyping uses genotype-specific antibodies and identifies genotypes indirectly. Two commercially available serologic genotyping assays have been introduced, including a RIBA SIA assay from Chiron Corp. and the Murex HCV serotyping enzyme immune assay from Nurex Diagnostics Ltd.

Sequences of genotype 4 HCV have been identified. For instance, GenBank accession # GU814266 represents a subgenomic genotype 4a replicon based on the ED43 infectious clone. Further discussion of the genotype 4 and their sequences are clinical impacts can be found at Zein *Clin. Microbiol. Rev.* 13(2):223-35 (2000).

The term "replicon" refers to a DNA molecule or RNA molecule, or a region of DNA or RNA, that replicates from a single origin of replication. For most prokaryotic chromosomes, the replicon is the entire chromosome. In some aspects, a replicon refers to a DNA or RNA construct that replicates in a cell in vitro. In one aspect, a replicon can replicate to produce at least about 10, or alternatively, at least about 100, 500, 1000, 2000, 5000, 10,000, $1\times10^5$, $1\times10^6$, $1\times10^7$, $1\times10^8$ or $1\times10^9$ copies of the replicon in a cell in vitro. Alternatively, a replicon's replication efficiency can be measured by producing certain amount of viral RNA in total RNA that includes cellular RNA. In one aspect, a replicon can produce at least about 1000, $1\times10^4$, $1\times10^5$, $1\times10^6$, $1\times10^7$, $1\times10^8$, $1\times10^9$, $1\times10^{10}$, $1\times10^{11}$, or $1\times10^{12}$ copies of the replicon per microgram of total RNA or cellular RNA.

A "subgenomic" HCV sequence refers to a HCV sequence that does not include all sequences of a wild-type HCV. In one aspect, a subgenomic HCV or a subgenomic HCV replicon does not include the E1, E2 or C regions. In another aspect, a subgenomic HCV or a subgenomic HCV replicon includes all or part of the 5' UTR, NS3, NS4A, NS4B, NS5A, NS5B and 3' UTR sequences. In contrast, a "full-length" or "full genome" HCV or HCV replicon includes E1, E2 and C regions. In some aspects, both a subgenomic and a full-length HCV replicon can include one or more of a reporter gene (e.g., luciferase), a marker gene (e.g., Neo), and an IRES (e.g., EMCV IRES) sequence.

A virus particle (or virion) consists of the genetic material made from either DNA or RNA of a virus and a protein coat that protects the genetic material. In one aspect, an envelope of lipids surrounds the protein coat when they are outside a cell.

The term "adaptive mutation" of a HCV replicon of a certain genotype refers to a mutation, as compared to a wild-type HCV sequence of the genotype, that enables the wild-type replicon to replicate in a cell, in particular in a eukaryotic cell such as a mammalian cell and in vitro, or enhances a HCV replicon's ability to replicate. It is contemplated that an adaptive mutation can favorably influence assembly of the replicase complex with host cell-specific protein, or alternatively promote interactions of the protein that includes the adaptive mutation (e.g., NS3, NS4A, NS4B, NS5A etc) with cellular proteins involved in host cell antiviral defenses.

A "reporter gene" refers to a gene that can be attached to a regulatory sequence of another gene of interest in cell culture, animals or plants, to facilitate identification of this other gene. Reporter genes are often used as an indication of whether a certain gene has been taken up by or expressed in the cell or organism population. Non-limiting examples of reporter gene include the luciferase gene and the green fluorescent protein gene.

A "marker gene" or "selectable marker" refers to a gene that protects the organism from a selective agent that would normally kill it or prevent its growth. One non-limiting example is the neomycin phosphotransferase gene (Neo), which upon expression confers resistance to G418, an aminoglycoside antibiotic similar in structure to gentamicin B1.

HCV Genotype 4 Replicon Constructs

The present disclosure relates, in general, to the unexpected discovery that clonal cell lines stably replicating genotype 4 replicons can be obtained by transcribing and electroporating subgenomic genotype 4 cDNAs into HCV permissive cell lines. From the clonal cells, adaptive mutations are then identified.

These adaptive mutations were located in NS3 (T343K/R, A200E, or T511R), NS4A (Q34K/R, or E52V) or NS5A (L179P). The S2204I (S232I within NS5A) mutation is also applicable in either genotypes. Identification of these mutations suggests that these mutations contribute to the HCV's capability to replicate in cells in vitro, a phenomenon not observed with wild-type HCV genotype 4 RNA. Such contribution has then been confirmed by engineering the mutations, by site-directed mutagenesis, into genotype 4 RNA and introducing them into the cell lines. Genotype 4 HCV RNA, with such mutations, successfully replicated in the cell lines. Therefore, the Applicant has demonstrated that the Applicant has prepared HCV genotype 4 replicons capable of replication in vitro and has identified adaptive mutations leading to such capabilities.

Accordingly, in one embodiment, the present disclosure provides a genotype 4 hepatitis C viral (HCV) RNA is capable of replication in a host cell. In one aspect, the replication is in vitro. In another aspect, the replication is productive. In another aspect, the cell is a eukaryotic cell such as a mammalian cell or a human cell. In yet another aspect, the cell is a hepatoma cell. In some aspects, the RNA can replicate to produce at least 10 copies of the RNA in a cell. In another aspect, the number of copies is at least about 100, 500, 1000, 2000, 5000, 10,000, $1\times10^5$, $1\times10^6$, $1\times10^7$, $1\times10^8$ or $1\times10^9$.

The HCV RNA can be a subgenomic HCV sequence. It is specifically contemplated that a full-length HCV replicon containing any or more of such adaptive mutations is also capable to replicate. Still further, an entire HCV virus of the corresponding genotype containing the adaptive mutation(s) would be infectious and capable to replicate. In any such case, RNA can include one or more of 5'NTR, an internal ribosome entry site (IRES), sequences encoding NS3, NS4A, NS4B, NS5A and NS5B, and a 3'NTR. In one aspect, the RNA includes, from 5' to 3' on the positive-sense nucleic acid, a functional HCV 5' non-translated region (5'NTR) comprising an extreme 5'-terminal conserved sequence; an HCV polyprotein coding region; and a functional HCV 3' non-translated region (3'NTR) comprising an extreme 3'-terminal conserved sequence.

In any of the above embodiments, the HCV RNA can include an adaptive mutation that enables the RNA to replicate in the cell. Such adaptive mutations can include an isoleucine at location 2204, which is residue 232 in NS5A.

Non-limiting examples of adaptive mutation for genotype 4 also include a glutamic acid at residue 200, a lysine or an arginine at residue 343, an arginine at residue 511, or combinations thereof for NS3, or a lysine or an arginine at residue 34, a valine at residue 52, or combinations thereof for NS4A, or yet a proline at residue 179 for NS5A.

Non-limiting examples of adaptive mutation for genotype 4 also include a serine at residue 607 for NS3.

In one embodiment, provided are replicons listed in Table 1. It is specifically contemplated that the HCV RNA can include one or more of the described mutations. In one aspect, the HCV RNA includes at least an adaptive mutation in NS3 and at least an adaptive mutation in NS4A. In another aspect, the HCV RNA includes at least an adaptive mutation in NS3 and at least an adaptive mutation in NS5A. In yet another aspect, the HCV RNA includes at least an adaptive mutation in NS4A and at least an adaptive mutation in NS5A.

Also contemplated are that the HCV RNA can be a RNA sequence that has at least about 75%, or about 80%, 85%, 90%, 95%, 98%, 99%, or about 99.5% sequence identity to any of the disclosed sequences, so long as it retains the corresponding adaptive mutation(s) and/or activities.

Thus, in one aspect, a genotype 4 HCV RNA construct is provided, comprising a 5'NTR, an internal ribosome entry site (IRES), sequences encoding NS3, NS4A, NS4B, NS5A and NS5B, and a 3'NTR, wherein the construct is capable to replicate in a eukaryotic cell. In one aspect, the construct comprises an adaptive mutation in NS3, NS4A, NS4B, NS5A or NS5B.

In one aspect, the mutation comprises an isoleucine at location 2204, which is residue 232 in NS5A. In another aspect, the mutation comprises, in NS3, a glutamic acid at residue 200, a lysine or an arginine at residue 343, an arginine at residue 511, or combinations thereof. Yet in another aspect, the mutation comprises, in NS4A, a lysine or an arginine at residue 34, a valine at residue 52, or combinations thereof. Further in an aspect, the mutation comprises, in NS5A, a proline at residue 179. In some aspect, the genotype 4 is genotype 4a.

In any of the above embodiments, the HCV RNA can further comprise a marker gene for selection. A non-limiting example of such marker gene is a neomycin phosphotransferase gene. Other examples are well known in the art.

In any of the above embodiments, the HCV RNA can further comprise a reporter gene. A non-limiting example of such marker gene is a luciferase gene. Other examples are well known in the art.

The RNA construct of any of the above embodiment can further comprise sequences encoding one or more of C, E1 or E2. In one aspect, the RNA construct is a full-length HCV replicon.

The disclosure also provides a single or double-stranded DNA that can be transcribed to a RNA construct of any of the above embodiment, a viral particle comprising a RNA construct of any of the above embodiment, or an isolated cell comprising a RNA construct of any of the above embodiment.

In one embodiment, the present disclosure provides an NS3 protein of HCV genotype 4 that comprises a glutamic acid at residue 200, a lysine or an arginine at residue 343, an arginine at residue 511, or combinations thereof.

In one embodiment, the present disclosure provides an NS4A protein of HCV genotype 4 that comprises a lysine or an arginine at residue 34, a valine at residue 52, or combinations thereof.

In one embodiment, the present disclosure provides an NS5A protein of HCV genotype 4 that comprises a proline at residue 179.

In one aspect of any such embodiments, the genotype 4 is genotype 4a. In yet another aspect, provided is a polynucleotide encoding the protein of any of such embodiments. The polynucleotide can be RNA or DNA. In another aspect, provided is an RNA or DNA construct comprising the polynucleotide. In yet another aspect, provided is a cell comprising the polynucleotide. Still in one aspect, provided is an antibody that specifically recognizes a protein of any of the above embodiments.

HCV Genotype 4 Replicons and Cells Containing the Replicons

Another embodiment of the present disclosure provides an isolated cell comprising a genotype 4 hepatitis C viral (HCV) RNA that replicates in the cell. In one aspect, there is an absence, in the cell, of a DNA construct encoding the RNA and thus copies of the HCV RNA are not transcribed from a DNA, such as cDNA, construct.

In one aspect, the cell comprises at least 10 copies of the RNA. In another aspect, the cell comprises at least 100, 500, 1000, 2000, 5000, 10,000, $1\times10^5$, $1\times10^6$, $1\times10^7$, $1\times10^8$ or $1\times10^9$ copies of the RNA.

The HCV RNA can be subgenomic HCV sequence or a full-length HCV sequence. In either case, RNA can include one or more of 5'NTR, an internal ribosome entry site (IRES), sequences encoding NS3, NS4A, NS4B, NS5A and NS5B, and a 3'NTR.

In any of the above embodiments, the HCV RNA can include an adaptive mutation that enables the RNA to replicate in the cell. Such adaptive mutations can include an isoleucine at location 2204, which is residue 232 in NS5A.

Non-limiting examples of adaptive mutation for genotype 4 also include a glutamic acid at residue 200, a lysine or an arginine at residue 343, an arginine at residue 511, or combinations thereof for NS3, or a lysine or an arginine at residue 34, a valine at residue 52, or combinations thereof for NS4A, or yet a proline at residue 179 for NS5A.

In one embodiment, provided are replicons listed in Table 1. It is specifically contemplated that the HCV RNA can include one or more of the described mutations. In one aspect, the HCV RNA includes at least an adaptive mutation in NS3 and at least an adaptive mutation in NS4A. In another aspect, the HCV RNA includes at least an adaptive mutation in NS3 and at least an adaptive mutation in NS5A. In yet another aspect, the HCV RNA includes at least an adaptive mutation in NS4A and at least an adaptive mutation in NS5A.

Also contemplated are that the HCV RNA can be a RNA sequence that has at least about 75%, or about 80%, 85%, 90%, 95%, 98%, 99%, or about 99.5% sequence identity to any of the disclosed sequences, so long as it retains the corresponding adaptive mutation(s).

In one aspect, the cell is a eukaryotic cell such as a mammalian cell and in particular a human cell. In another aspect, the cell is hepatoma cell, such as but not limited to a Huh7 cell (e.g., Huh7-Lunet, 51C and 1 C). It is herein discovered surprisingly that Huh7 1C cell is particularly permissive to the genotype 4 replicons and thus in one aspect, the cell is a Huh7 1C cell. In some aspects, the cell is placed at an in vitro or ex vivo condition.

Methods of Preparing Genotype 4 Replicons

After HCV genotype 4 replicons are identified, as shown in Example 1, introduction of the relevant adaptive mutation into a corresponding genotype HCV RNA can result in the RNA's capability to replicate, in particular in a mammalian cell in vitro. Accordingly, the present disclosure provides a method of improving the capability of a genotype 4 HCV viral RNA to replicate in a eukaryotic cell, comprising one or more of:

(a) substituting residue 200 of NS3 with a glutamic acid,
(b) substituting residue 343 of NS3 with a lysine or an arginine,
(c) substituting residue 511 of NS3, with an arginine,
(d) substituting residue 34 of NS4A with a lysine or an arginine,
(e) substituting residue 52 of NS4A with a valine, or
(f) substituting residue 179 of NS5A with a proline. In one aspect, the method comprises at least two substitutions of (a)-(f).

In any of the above methods, an S2204I (S232I within NS5A) mutation can further be introduced into the RNA.

Methods of Screening HCV Inhibitors Targeting Genotype 4

Numerous known and unknown HCV inhibitors have been tested for their efficiency in inhibiting the genotype 4 HCV, in comparison with genotype 1b (Example 1). Some showed higher efficacy for genotype 4, and some were not as efficacious. The usefulness of the new identified genotype 4 replicons, therefore, is adequately demonstrated.

Thus, the present disclosure also provides, in one embodiment, a method of identifying an agent that inhibits the replication or activity of a genotype 4 HCV, comprising contacting a cell of any embodiment of the present disclosure with a candidate agent, wherein a decrease of replication or a decrease of activity of a protein encoded by the RNA indicates that the agent inhibits the replication or activity of the HCV. In some aspects, the protein is a protease, such as any or more of NS3, NS4A, NS4B, NS5A or NS5B. Replication of the RNA, in one aspect, can be measured by a reporter gene on the RNA, such as the luciferase gene.

Provided in another embodiment is a method of identifying an agent that the activity of a genotype 4 HCV, comprising contacting the lysate of a cell of any embodiment of the present disclosure with a candidate agent, wherein a decrease of the activity of a protein encoded by the RNA indicates that the agent inhibits the activity of the HCV. In one aspect, the protein is a protease, such as any or more of NS3, NS4A, NS4B, NS5A or NS5B. In another aspect, the method further comprises measuring the replication of the RNA or the activity of the protein encoded by the RNA.

A HCV inhibitor (or "candidate agent") can be a small molecule drug that is an organic compound, a peptide or a protein such as antibodies, or nucleic acid-based such as siRNA. In May 2011, the Food and Drug Administration approved 2 drugs for Hepatitis C, boceprevir and telaprevir. Both drugs block an enzyme that helps the virus reproduce. Boceprevir is a protease inhibitor that binds to the HCV NS3 active site on hepatitis C genotype 1. Telaprevir inhibits the hepatitis C virus NS3.4A serine protease.

More conventional HCV treatment includes a combination of pegylated interferon-alpha-2a or pegylated interferon-alpha-2b (brand names Pegasys or PEG-Intron) and the antiviral drug ribavirin. Pegylated interferon-alpha-2a plus ribavirin may increase sustained virological response among patients with chronic hepatitis C as compared to pegylated interferon-alpha-2b plus ribavirin according to a systematic review of randomized controlled trials.

All of these HCV inhibitors, as well as any other candidate agents, can be tested with the disclosed methods for their efficacy in inhibiting HCV genotype 4. The cells are then incubated at a suitable temperature for a period time to allow the replicons to replicate in the cells. The replicons can include a reporter gene such as luciferase and in such a case, at the end of the incubation period, the cells are assayed for luciferase activity as markers for replicon levels. Luciferase expression can be quantified using a commercial luciferase assay.

Alternately, efficacy of the HCV inhibitor can be measured by the expression or activity of the proteins encoded by the replicons. One example of such proteins is the NS3 protease, and detection of the protein expression or activity can be carried out with methods known in the art, e.g., Cheng et al., *Antimicrob Agents Chemother* 55:2197-205 (2011).

Luciferase or NS3 protease activity level is then converted into percentages relative to the levels in the controls which can be untreated or treated with an agent having known activity in inhibiting the HCV. A decrease in HCV replication or decrease in NS3 activity, as compared to an untreated control, indicates that the candidate agent is capable of inhibiting the corresponding genotype of the HCV. Likewise, a larger decrease in HCV replication or larger decrease in NS3 activity, as compared to a control agent, indicates that the candidate is more efficacious than the control agent.

EXAMPLES

The present disclosure is further defined by reference to the following examples. It will be apparent to those skilled in the art that many modifications, both to threads and methods, may be practiced without departing from the scope of the current disclosure.

Abbreviations

Unless otherwise stated all temperatures are in degrees Celsius (° C.). Also, in these examples and elsewhere, abbreviations have the following meanings:

| | |
|---|---|
| μF = | MicroFaraday |
| μg = | Microgram |
| μL = | Microliter |
| μM = | Micromolar |
| g = | Gram |
| hr = | Hour |
| mg = | Milligram |
| mL = | Milliliter |
| mM = | Millimolar |
| mmol = | Millimole |
| nM = | Nanomolar |
| nm = | Nanometer |
| pg = | pictograms |
| DMEM = | Dulbecco's modified Eagle's medium |
| EMCV = | encephalomyocarditis virus |
| FBS = | fetal bovine serum |
| HCV = | Hepatitis C virus |
| IRES = | internal ribosome entry site |
| rpm = | revolutions per minute |
| RT-PRC = | reverse transcription-polymerase chain reaction |

Example 1

Generation of Robust Genotype 4 Hepatitis C Virus Subgenomic Replicons

This example shows that adaptive mutations were identified from genotype 4 HCV viral replicons capable of replication in Huh7 cells and that HCV replicons with these adaptive mutations are useful tools for antiviral drug screening.
Materials and Methods
Cell Culture Three HCV permissive cell lines were used during these studies: Huh7-Lunet, 51C, and 1C. Huh7-lunet was obtained from ReBLikon GmbH (Mainz, Germany) (Friebe et al., *J Virol* 79:380-92 (2005)). The derivation of 51C cells, and stable genotype 1a H77 and genotype 1b Con-1 Rluc-Neo replicon cells were previously described (see Robinson et al., *Antimicrob Agents Chemother* 54:3099-106 (2010)). 1C cells were derived by curing a GS-5885-resistant genotype 1a replicon clone derived from 51C cells (id.). This clonal line showed the highest permissivity to GT1a and 1b replicons out of screened 50 clones and was 5-10 folds more permissive than Huh7-Lunet and 51C cells overall. All cell lines were propagated in Dulbecco's modified Eagle's medium (DMEM) with GlutaMAX-I (Invitrogen, Carlsbad, Calif.) supplemented with 10% fetal bovine serum (FBS; HyClone, Logan, Utah), 1 unit/ml penicillin (Invitrogen), 1 μg/ml streptomycin (Invitrogen), and 0.1 mM non-essential amino acids (Invitrogen); this media formulation is referred to as complete DMEM. Replicon cell lines were selected and maintained in complete DMEM containing 0.5 mg/ml G418 (also known as Geneticin®, an aminoglycoside antibiotic, Invitrogen).
Construction of Plasmids Encoding Genotype 4a HCV Subgenomic Replicons A plasmid (pGT4aED43SG) encoding a subgenomic genotype 4a replicon based on the ED43 infectious clone (GenBank accession # GU814266, SEQ ID NO: 8, which encodes polyprotein sequence profvided in GenBank accession # ADF97234, SEQ ID NO: 9) (Chamberlain et al., *J Gen Virol* 78 (Pt 6):1341-7 (1997); Gottwein et al., *J Virol* 84:5277-93 (2010)) was prepared by DNA synthesis and cloning (Genescript, Piscataway, N.J.). The synthesized replicon incorporated following elements from 5' to 3' (FIG. 1): (1) the ED43 5'UTR, extending to the first 48 nucleotides of core, (2) a linker with the nucleotide sequence, 5'-GGCGCGCCA-3' (SEQ ID NO: 1) which introduces the AscI restriction site (underlined), (3) the neo gene, (4) a linker with nucleotide sequence, 5'-GGCCGGCCGCGGCCGCAA-3' (SEQ ID NO: 2) which introduces FseI and Not I restriction sites (underlined), (5) the encephalomyocarditis virus (EMCV) IRES, (6) a linker with nucleotide sequence 5'-ACGCGTATG-3' (SEQ ID NO: 3) which introduces the MluI restriction site (underlined) and an ATG start codon for HCV polyprotein expression, (7) the NS3-NS5B polyprotein region of ED43 including an NS5A adaptive mutation (S2204I, or S232I within NS5A) and (8) the 3'UTR of ED43. The synthetic DNA fragment encoding the ED43 replicon was inserted into PUC19 between EcoRI and XbaI restriction sites.

Another plasmid (pGT4aED43RlucSG) encoding a subgenomic replicon that incorporated the humanized Renilla luciferase reporter gene was generated as follows: The pGT4aED43SG plasmid (described above) was cut using AscI and MluI restriction enzymes (to remove the neo gene) and gel purified using a commercial kit (Qiagen). A gene fragment encoding the humanized Renilla luciferase gene fused with the neo gene along with the EMCV region, were PCR amplified by using Accuprime super mix I (Invitrogen) with the following primers from the phRlucNeoSG2a plasmid described below: 2aRlucNeoAsclFor: 5'-AACACCAACGGCGCGCCAATGGCTTCCAAGGTGTAC-3' (SEQ ID NO: 4, AscI site is introduced by the primer and is underlined), 2aEMCVIRESM1uIRev: 5'-TGGGCATAAGCAGTGATGGGAGCCATACGCGTATCG -3' (SEQ ID NO: 5, MluI site underlined).

Plasmid phRlucNeoSG2a was derived from the plasmid pLucNeo2a (Cheng et al., *Antimicrob Agents Chemother* 55:2197-205 (2011)). The hRenilla Luciferase-Neomycin fusion gene (hRluc-Neo) was PCR amplified from pF9 CMV hRluc-neo Flexi(R) (Promega, Madison, Wis.) by PCR using Accuprime Super Mix I (Invitrogen) and a primer set of AfeI hRLuc Fwd and NotI Neo Rev. These two primers had the following sequence and introduced restriction sites for subsequent cloning: AfeI hRLuc: 5' AT AGCGCTATGGCTTCCAAGGTGTACGA 3' (SEQ ID NO: 6, AfeI site underlined), NotI Neo Rev: 5' AAT GCGGCCGCTCAGAAGAACTCGTCA 3' (SEQ ID NO: 7, NotI site underlined). The hRluc-Neo amplification product was subcloned into pCR2.1-TOPO (Invitrogen). The resulting plasmid was digested with AfeI and NotI, and the excised fragment (hRluc-Neo) was ligated with T4 DNA ligase (Promega) into pLucNeo2a digested with the same enzymes. The resulting vector, phRlucNeoSG2a, was sequenced to ensure correct orientation and sequence of the hRluc-Neo fusion gene.

The subsequent PCR fragment was cut with AscI and MluI and gel purified using a commercial kit (Qiagen). The vector and insert pieces were ligated using LigaFast Rapid DNA Ligation System per manufacturer's protocol (Promega). The resulting vector, pGT4aED43RlucSG was sequenced to confirm the correct orientation and sequence of the hRluc-Neo.

Construction of Mutant Replicons

Adaptive mutations were introduced into the pGT4aED43RlucNeoSG replicon by site directed mutagenesis using a QuikChange Lightening kit (Stratagene, La Jolla, Calif.). All mutations were confirmed by DNA sequencing by TACGen (Hayward, Calif.).

RNA Transcription

Plasmids encoding genotype 4a subgenomic HCV replicons were linearized with XbaI and purified using a PCR purification kit (Qiagen). RNA was synthesized and purified with T7 MEGAScript (Ambion, Austin, Tex.) and RNeasy kits, respectively, according to the manufacturer's instructions. RNA concentrations were measured using optical density at 260 nm and confirmed by 0.8% agarose gel electrophoresis (Invitrogen).

RNA Transfection and Isolation of Stable Replicon Cell Lines

Ten micrograms of in vitro-transcribed RNA were transfected into Huh7-Lunet, 51C, or 1C cells by electroporation as previously described (Robinson et al., *Antimicrob Agents Chemother* 54:3099-106 (2010)). Briefly, cells were collected by trypsinization and centrifugation, then washed twice with ice-cold phosphate buffered saline (PBS) and resuspended in Opti-MEM medium (Invitrogen) at a concentration of $10^7$ cells/ml. Replicon RNA was added to 400 μl of cell suspension in a Gene Pulser (BioRad, Hercules, Calif.) cuvette (0.4-cm gap). Cells were electroporated at 270 V and 960 μF, incubated at room temperature for 10 minutes, resuspended in 30 ml complete DMEM and then plated into 100-mm-diameter dishes. Forty-eight hours after plating, medium was replaced with complete DMEM supplemented with 0.5 mg/ml G418 which was refreshed twice per week. Cell clones were isolated after approximately three weeks of G418 selection, expanded, and cryopreserved at early passages.

Replicon Colony Formation Assays

To determine the efficiency of G418-resistant colony formation, cells were electroporated with indicated amounts of replicon RNA or cellular RNA extract, and plated at multiple densities ranging from $2 \times 10^5$ to $2 \times 10^6$ cells/100 mm dish. Forty-eight hours after plating, medium was replaced with complete DMEM supplemented with 0.5 mg/ml G418 which was refreshed twice per week. Three weeks later, colony plates were used for cell expansion or G418-resistant foci were fixed with 4% formaldehyde and stained with 0.05% crystal violet in $H_2O$.

Extraction, Amplification, and Genotypic Analysis of HCV RNA

HCV RNA isolation, RT-PCR, and sequencing were performed by TACGen (Hayward, Calif.). HCV replicon cellular RNA was extracted and purified using an RNeasy kit (Qiagen) according to the manufacturer's protocol. RT-PCR was performed using the SuperScript III first-strand synthesis system (Invitrogen). PCR products were sequenced by TACGen (Hayward, Calif.).

Detection of NS5A protein by indirect immunofluorescence

Replicon cells were plated in 96-well plates at a density of $1 \times 10^4$ cells per well. After cultured for 24 hours, cells were then stained for NS5A protein as described previously (Cheng et al., *Antimicrob Agents Chemother* 55:2197-205 (2011)). Briefly, cells were fixed in 4% paraformaldehyde for 20 minutes. Cells were then washed three times with PBS, blocked with 3% bovine serum albumin, 0.5% Triton X-100, and 10% FBS and then stained with anti-NS5A antibody. Staining was performed using a 1:10,000 dilution of mouse monoclonal antibody 9E10 (Apath, Brooklyn, N.Y.). After washing in PBS three times, a secondary anti-mouse antibody conjugated to Alexa Fluor 555 was used to detect anti-NS5A antibody labeled cells (Invitrogen). Nuclei were stained with 1 μg/ml Hoechst 33342 (Invitrogen). Cells were washed with PBS and imaged with a Zeiss fluorescence microscope (Zeiss, Thornwood, N.Y.).

Replicon cell NS3 protease assay for replicon RNA replication

Genotype 4a clonal replicons cells were seeded in 96-well plates at a concentration of $1 \times 10^4$ cells per well. The cells were incubated for 24 hours, after which culture media were removed. The replicon cells were then lysed with 90 μl of 1× Promega luciferase lysis buffer supplemented with 150 mM NaCl at room temperature for 20 min on a plate shaker. 10 μl of 1 μM europium-labeled NS3 substrate in the above lysis buffer was added to each well. Protease activity data were collected and analyzed as previously described (Cheng et al., *Antimicrob Agents Chemother* 55:2197-205 (2011)).

Replicon Antiviral Assays 2,000 cells/well were seeded in 384-well plates in 90 μl of DMEM culture medium, excluding G418. HCV inhibitors (Compounds A-E, available from Gilead Sciences, Inc, Foster City, Calif.) were added to cells at a 1:225 dilution, achieving a final concentration of 0.44% in a total volume of 90.4 μl. Three-fold serial drug dilutions with 10 concentrations were used, and starting concentrations were 4.4 μM or 0.44 μM for all the tested compounds, except Compound A whose starting concentrations was 44.4 nM. Cell plates were incubated at 37° C. for 3 days, after which culture medium was removed and cells were assayed for luciferase activity as markers for replicon levels. Luciferase expression was quantified using a commercial luciferase assay (Promega). Luciferase or NS3 protease activity levels were converted into percentages relative to the levels in the untreated controls (defined as 100%), and data were fitted to the logistic dose response equation y_a/[1_(x/b)c] using XLFit4 software (IDBS, Emeryville, Calif.) (y is the amount of normalized luciferase signal, x is the drug concentration, a represents the curve's amplitude, b is the x value at its transition center [$EC_{50}$], and c is a parameter which defines its transition width).

Results

Adaptive Mutations

Figure 2:
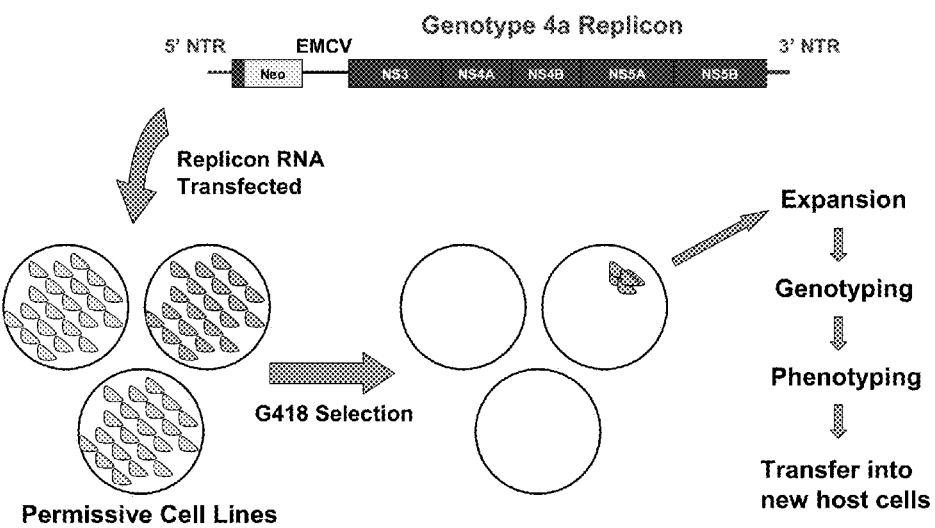
FIG. 2 is a schematic diagram of genotype 4a replicon establishment strategy.
Figure 3:
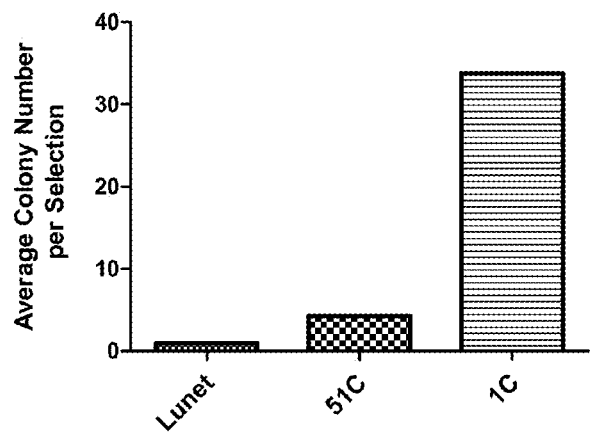
FIG. 3 shows the numbers of surviving colonies in three different cell lines. Huh-7 Lunet, 51C and 1C cells were transfected with the GT4a replicon RNA respectively as described in the Materials and Methods. The numbers of surviving colonies were counted for each selection. The data represent an average of at least 6 independent transfections. Huh7-lunet was obtained from ReBLikon GmbH (Mainz, Germany). The derivation of 51C cells was previously described (Robinson et al., *Antimicrob Agents Chemother* 54:3099-106 (2010)). 1C cells were derived by curing a GS-5885-resistant genotype 1a replicon clone derived from 51C cells. GS-5885 is an NS5A inhibitor, available from Gilead Sciences, Inc. Foster City, Calif. The figure shows that Huh7 1C cells were more permissive than Huh7-Lunet or 51C cells to GT4a replicon replication.
Figure 4:
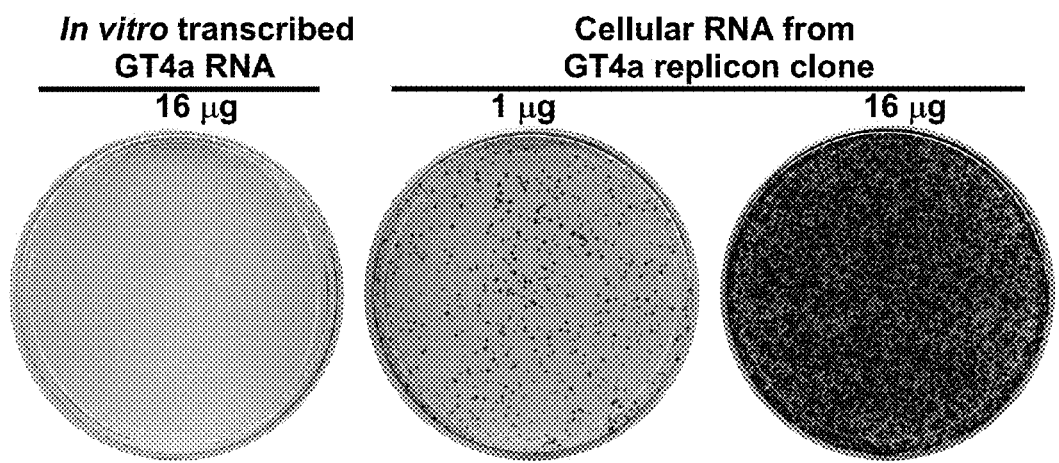
FIG. 4 shows that selected GT4a replicon clones acquired adaptive genetic changes. Total cellular RNA was extracted from a primary genotype 4a replicon cell clone then electroporated into Huh-7 Lunet cells at the indicated amounts. Transfected cells were resuspended in complete DMEM medium and plated at multiple densities ranging from $2 \times 10^5$ to $2 \times 10^6$ cells in a 100 mm-diameter dish. Forty-eight hours after plating, medium was replaced with complete DMEM supplemented with 0.5 mg/ml G418 which was refreshed twice per week. Three weeks later, colony plates were fixed with 4% formaldehyde and stained with 0.05% crystal violet in $H_2O$. In vitro transcribed GT4a replicon RNA was transfected in parallel as a control. The greatly enhanced colony formation efficiency of the RNA extracted from the primary genotype 4 replicon indicates that the replicons in that clone had acquired adaptive changes that allowed robust replication in vitro.

Using the strategy as illustrated in FIG. 2, a number of GT4a colonies were obtained. RNA was then extracted from these colonies. As shown in FIG. 3, Huh7 1C cells were more permissive than Huh7-Lunet or 51C cells to GT4a replicon replication. Using Huh7-Lunet cells, the colony formation capabilities of the GT4a replicons were tested and compared to the original GT4a RNA. As shown in FIG. 4, greatly enhanced colony formation efficiency of the RNA extracted from the GT4a colonies indicates that the replicons acquired adaptive changes that allowed robust replication in vitro.

Figure 5:
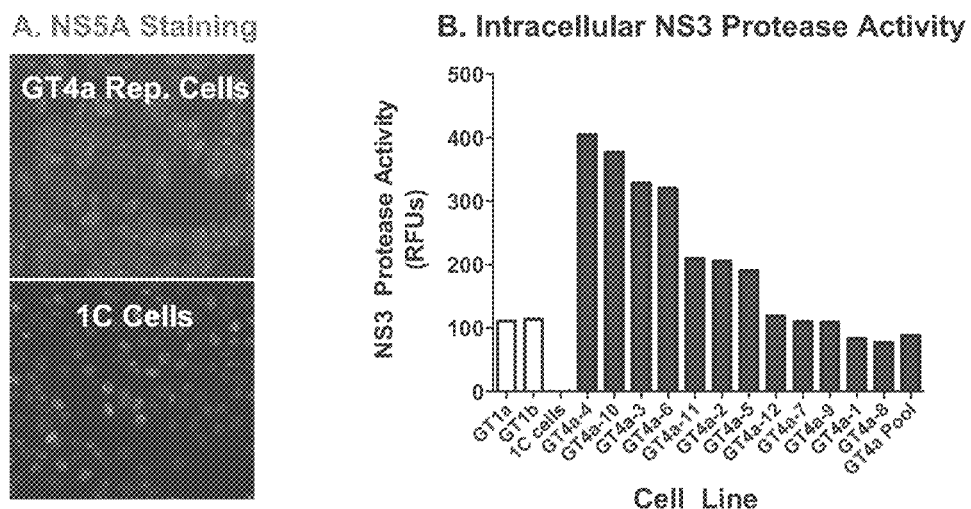
FIG. 5 shows robust NS5A and NS3 expression in GT4a replicon cell lines (A). A GT4a replicon cell pool was stained with anti-NS5A antibody (Apath, Brooklyn, N.Y.; upper panel, light gray) and Hoechst 33342 (Invitrogen; 1 μg/ml) (lower panel, dark gray indicates nuclei). 1C cells were stained as a negative control (lower panel). GT4a replicon cells were clearly positive for NS5A indicating active replication. (B) Selected GT4a replicon cell lines were measured for their intracellular NS3 protease activity as described in Materials and Methods. GT1a and GT1b stable replicon cells were included for comparison of the NS3 protease activity. 1C cells were included as a negative control. Robust NS3 activity, indicating robust replicon activity, was observed in the GT4a replicon cell lines with some GT4a replicon cell lines exceeding the NS3 signal produced by standard GT1a and 1b replicon cells.

The expression of NS5A and NS3 proteins were then examined to confirm the replication of the GT4a replicons. Stained with anti-NS5A antibodies, GT4a replicon cells were clearly positive for NS5A which indicated active replication (FIG. 5A). In the same vein, robust NS3 activity, indicating robust replicon activity, was observed in the GT4a replicon cell lines with some GT4a replicon cell lines exceeding the NS3 signal produced by standard GT1a and 1b replicon cells, which were used as positive controls (FIG. 5B). Apparently, the GT4b replicons were actively replicating in the cells.

Figure 6:
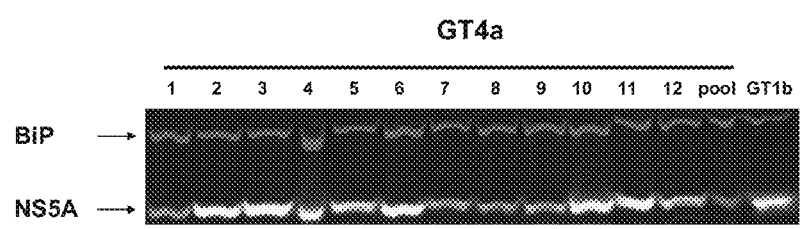
FIG. 6 confirms robust NS5A expression in GT4a replicon cell lines. Stable GT4a and GT1b replicon cells, $0.5 \times 10^6$ each, were pelleted and completely lysed in 100 μl SDS loading buffer. 12 μl lysates were subjected to SDS-PAGE and Western blot analysis. The blot was stained with primary anti-NS5A antibody (Apath; 1:10000 dilution) and secondary anti-mouse antibody (IRDye 800CW Goat anti-Mouse IgG (H+L) from LI-COR, 1:10,000 dilution). The staining was then analyzed by Odyssey Imaging (LI-COR. Lincoln, Nebr.). The blot was also co-stained with anti-BiP antibody (Abcam; 1:1000 dilution) and secondary anti-rabbit antibody (IRDye 800CW Goat anti-Rabbit IgG (H+L) from LI-COR, 1:10,000 dilution) as a loading control. Strong expression of NS5A was detected in the GT4a replicon cell clones, confirming that these cells stably and robustly replicate this replicon, either exceeding or being comparable to the NS5A expression level by standard GT1b replicon cells.

Moreover, when the GT4a colonies were lysed, strong expression of NS5A was detected in the cell lysates (FIG. 6), confirming that these cells stably and robustly replicated GT4a replicon, either exceeding or being comparable to the NS5A expression level of standard GT1b replicon cells.

Selected GT4a replicon cell lines or pooled cell lines were expanded and subjected to genotypic analysis. Total RNA was extracted and purified using an RNeasy kit (Qiagen) according to the manufacturer's protocol. RT-PCR was performed using the SuperScript III first-strand synthesis system (Invitrogen). PCR products were sequenced by TACGen. Novel mutations that emerged during adaptation of the GT4 replicon are presented in Table 1.

TABLE 1

Mutations identified in GT4a replicon cells

| Clone # | NS3 | NS4A | NS5A |
| --- | --- | --- | --- |
| 1 | T343K | | |
| 2 | | Q34K | |
| 3 | T343K | | |
| 4 | | Q34K | |
| 5 | | E52V | |
| 6 | T343R | | |
| 7 | A200E | | |
| 8 | A200E | | |
| 9 | | Q34R | |
| 10 | T511R | | L179P |
| 11 | T343K | | |
| 12 | | Q34R | |
| Pooled | A200A/E | Q34R/K | |

Figure 7:
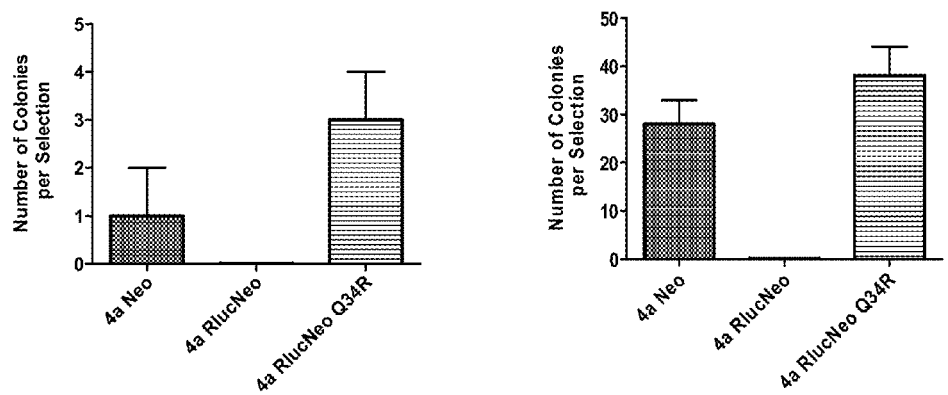
FIG. 7 shows that NS4A Q34R is a cell culture adaptive mutation for GT4a replication. The Neo gene of the GT4a ED43-neo construct was replaced with a Rluc-neo fusion reporter to facilitate the measurement of replicon replication in the cell culture (by luciferase). The Q34R mutation in the NS4A gene was then introduced into the GT4a ED43-Rluc-Neo construct by site-directed mutagenesis. All three replicon RNAs were transfected into Huh7-Lunet (left panel) and 1C (right panel) cells respectively. The number of surviving colonies was counted for each selection. The data represent an average of at least two independent transfections. The Q34R mutation enabled the GT4a ED43-RlucNeo to establish colonies whereas the same replicon without this mutation does not establish colonies. A clone of GT4a RlucNeoQ34R was selected due to its higher Rluc signal and amplified for antiviral assays.

These mutations were then tested by introducing them, by site-directed mutagenesis, into the original GT4a RNA. FIG. 7 shows that, in both Huh7-Lunet (left panel) and 1C (right panel) cells, the GT4a RNA with the Q34R mutation enabled the GT4a ED43-RlucNeo to establish colonies whereas the same replicon without this mutation does not establish colonies.

Figure 8:
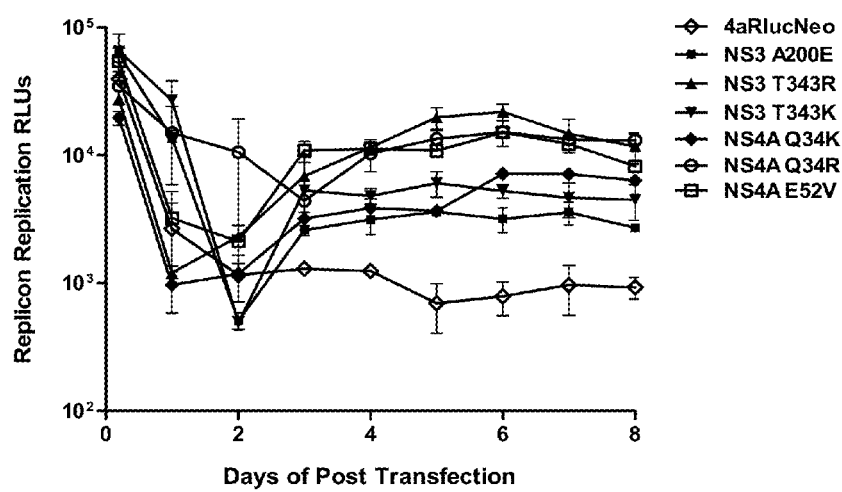
FIG. 8 presents data to show that the NS3 A200E, T343R and T343K and NS4A Q34R, Q34K and E52V mutations are cell culture adaptive mutations for GT4a replication. The Neo gene of the GT4a ED43-neo construct was replaced with a Rluc-neo fusion reporter to facilitate the measurement of replicon replication in the cell culture (by luciferase). Mutations A200E, T343R and T343K in the NS3 gene and Q34K, Q34R and E52V in the NS4A gene were then introduced into the GT4a ED43-RlucNeo construct by site-directed mutagenesis respectively. All replicon RNAs were transfected into 1C cells individually and $1 \times 10^4$ transfected cells were plated into a well in a 96-well plate. At 4 h and day 1 to day 8 daily post transfection, cells were analyzed for renilla luciferase activity. Cells were passaged and replated at day 4. At each time point, quadruple wells were assayed for each transfection and the data represents an average of two independent experiments with error bars. All tested mutations, A200E, T343R and T343K in the NS3 gene and Q34K, Q34R and E52V in the NS4A gene, significantly enhanced GT4a ED43-RlucNeu replication as evidenced by the increase of Rlu signal from day 2 after initial decrease of the signal derived from the direct translation of input RNA that was independent of RNA replication. In contrast, the same replicon without a mutation did not show any meaningful replication.

Likewise, the ability of NS3 A200E, T343R and T343K and NS4A Q34R, Q34K and E52V mutations to enable GT4a to establish colonies were also confirmed in Huh7 1C cells (FIG. 8). FIG. 8 shows that all tested mutations, A200E, T343R and T343K in the NS3 gene and Q34K, Q34R and E52V in the NS4A gene, significantly enhanced GT4a ED43-RlucNeo replication as evidenced by the increase of Rluc signal from day 2 after initial decrease of the signal derived from the direct translation of input RNA that was independent of RNA replication. In contrast, the same replicon without a mutation did not show any meaningful replication.

Following the identification of the genotype 4 replicons containing adaptive mutations, the usefulness of these replicons in screening antiviral agents were evaluated with a variety of anti-HCV agents. Different classes of HCV inhibitors that target NS5A, NS5B active site, NS3 protease, NS5B non-active sites, NS4A and host factors, were evaluated for their antiviral activities against stable genotype 1b and genotype 4a Rluc-Neo replicon cells carrying NS4A Q34R mutation.

Like in stable genotype 1b replicon cells, $EC_{50}$ values against the genotype 4a replicon were generated successfully for all the inhibitors in a high throughput 384-well format by measuring renilla luciferase activity. The inhibition data are listed in Table 2 and indicate that Compound B was potent against both genotype 1b and 4a replicons with comparable $EC_{50}$ values. Further, Compound A remained potent though it lost 50-fold potency against GT4a.

However, Compound D and Compound E lost their activities approximately 1000-and 10-folds respectively. Compound C remained potent against genotype 4a replicon, with a minor loss (1.5-3 fold) of their potency compared to their activities against genotype 1b replicon.

These results demonstrate this novel genotype 4a Rluc-Neo replicon could serve as a valuable tool for drug discovery and lead compound optimization against HCV genotype 4a.

TABLE 2

Comparison of antiviral activities or HCV inhibition against genotype 1b and 4a replicons

| Compounds | GT1b RLucNeo EC50 (nM) | GT4a RlucNeo EC50 (nM) |
| --- | --- | --- |
| Compound A | 0.002 | 0.105 |
| Compound B | 117.3 | 0.61 |
| Compound C | 7.0 | 10.1 |
| Compound D | 0.47 | 469.4 |
| Compound E | 0.55 | 6.4 |

Here the Applicant reports the isolation of the first genotype 4 replicons that efficiently replicate in vitro. It is demonstrated that robust replication requires adaptive mutations in NS3 or NS4A in conjunction with NS5A. By incorporating adaptive mutations into luciferase encoding constructs, Applicant was able to generate genotype 4 replicon cell clones that will enable one to profile antiviral compounds. These replicon cells should also serve as valuable tools for molecular virology studies and the characterization of resistance mutations emerging in HCV genotype 4 patients.

In summary, subgenomic replicon cDNAs based on the genotype 4a strain ED43 were synthesized, cloned, transcribed and electroporated into HCV permissive cell lines. Clonal cell lines stably replicating genotype 4a replicons were selected with G418. Adaptive mutations were identified by RT-PCR amplification and DNA sequencing and engineered into the parental replicons by site-directed mutagenesis.

Numerous electroporations into multiple different permissive cell lines allowed the identification of a few colonies that replicated genotype 4 replicons. Expansion and sequencing of these replicons clones revealed adaptive mutations in viral proteins. These adaptive mutations were located in NS3 (T343K/R, A200E, or T511R), NS4A (Q34K/R, or E52V) or NS5A (L179P). These adaptive mutations were engineered back into the parental ED43 strain and were able to greatly enhance replication and colony formation efficiency.

The establishment of robust genotype 4 replicon systems provides powerful tools to facilitate drug discovery and development efforts. Use of these novel replicons in conjunction with those derived from other genotypes will aid in the development of pan-genotypic HCV regimens.

Example 2

Screening of New HCV Inhibitors for Genotype 4

Example 1 shows that agents known to be HCV inhibitors for other genotypes, such as genotype 1, can be tested with the genotype 4 replicons for their efficacy in inhibiting genotype 4 HCV. It is also contemplated that agents not yet known to be inhibitory of HCV can be screened with these genotype 4 replicons as well.

The candidate HCV inhibitor can be a small molecule drug, a peptide or a protein such as antibodies, or nucleic acid-based such as siRNA. The candidate HCV inhibitor is incubated with cells that contain a genotype 4 replicon, at a suitable temperature for a period time to allow the replicons to replicate in the cells. The replicons can include a reporter gene such as luciferase and in such a case, at the end of the incubation period, the cells are assayed for luciferase activity as markers for replicon levels. Luciferase expression can be quantified using a commercial luciferase assay. Alternately, efficacy of the HCV inhibitor can be measured by the expression or activity of the proteins encoded by the replicons. One example of such proteins is the NS3 protease, and detection of the protein expression or activity can be carried out with methods known in the art, e.g., Cheng et al., *Antimicrob Agents Chemother* 55:2197-205 (2011).

Luciferase or NS3 protease activity level is then converted into percentages relative to the levels in the controls which can be untreated or treated with an agent having known activity in inhibiting the HCV. A decrease in HCV replication or decrease in NS3 activity, as compared to an untreated control, indicates that the candidate agent is capable of inhibiting the corresponding genotype of the HCV. Likewise, a larger decrease in HCV replication or larger decrease in NS3 activity, as compared to a control agent, indicates that the candidate is more efficacious than the control agent.

It will be appreciated that those skilled in the art will be able to devise various arrangements which, although not explicitly described or shown herein, embody the principles of the disclosure and are included within its spirit and scope. Furthermore, all conditional language recited herein is principally intended to aid the reader in understanding the principles of the disclosure and the concepts contributed by the inventors to furthering the art, and are to be construed as being without limitation to such specifically recited conditions. Moreover, all statements herein reciting principles, aspects, and embodiments of the disclosure are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

---

The invention claimed is:

1. An isolated genotype 4a hepatitis C viral (HCV) RNA construct comprising a 5'NTR, an internal ribosome entry site (IRES), sequence encoding one or more of NS3, NS4A, NS4B, NS5A or NS5B, and a 3'NTR, wherein the RNA construct further comprises a mutation as compared to a wild-type HCV 4a sequence of SEQ ID NO:8, wherein said mutations is T343K, T343R, A200E, or T511R in NS3, or Q34K, Q34R, or E52V in NS4A, or L179P in NS5A, and wherein the mutation positions correspond to the residue positions in SEQ ID NO:9.

2. The RNA construct of claim 1, wherein the construct further comprises a S232I mutation in NS5A as compared to a wild-type HCV 4a sequence.

3. The RNA construct of claim 1, wherein the mutation is T343K, T343R, A200E, or T511R in NS3, or combinations thereof.

4. The RNA construct of claim 1, wherein the mutation is Q34K, Q34R, or E52V in NS4A, or combinations thereof.

5. The RNA construct of claim 1, wherein the RNA construct comprises the mutation L179P in NS5A.

6. The RNA construct of claim 1, wherein the construct comprises at least one said mutation in NS3 and at least one said mutation in NS4A.

7. The RNA construct of claim 1, wherein the construct comprises at least one said mutation in NS3 and said mutation in NS5A.

8. The RNA construct of claim 1, wherein the construct comprises at least one said mutation in NS4A and said mutation in NS5A.

9. The RNA construct of claim 1, wherein the construct comprises at least one said mutation in NS3A, at least one said mutation in NS4A, and said mutation in NS5A.

10. The RNA construct of claim 1, further comprising a marker gene for selection.

11. The RNA construct of claim 10, wherein the marker gene is a neomycin phosphotransferase gene.

12. The RNA construct of claim 1, further comprising a reporter gene.

13. The RNA construct of claim 12, wherein the reporter gene is luciferase.

14. The RNA construct of claim 1, wherein the construct comprises, from 5' to 3', the 5'NTR, the IRES, sequence encoding NS3, NS4A, NS4B, NS5A and NS5B, and the 3'NTR.

15. The RNA construct of claim 1, further comprising a sequence encoding one or more of C, E1 or E2.

16. An isolated cell comprising the RNA construct of claim 1.

17. The cell of claim 16, wherein the cell is a mammalian cell.

18. The cell of claim 17, wherein the cell is a hepatoma cell.

19. The cell of claim 18, wherein the cell is a Huh7 1C cell.

20. The RNA construct of claim 1, wherein the RNA construct is capable of replication in the eukaryotc cell in vitro.

* * * * *

UNITED STATES PATENT AND TRADEMARK OFFICE
CERTIFICATE OF CORRECTION

| | | |
|---|---|---|
| PATENT NO. | : 8,889,849 B2 | Page 1 of 1 |
| APPLICATION NO. | : 13/542554 | |
| DATED | : November 18, 2014 | |
| INVENTOR(S) | : Delaney, IV et al. | |

It is certified that error appears in the above-identified patent and that said Letters Patent is hereby corrected as shown below:

IN THE SPECIFICATION:

Column 1, Line 13, replace "LISING" with --LISTING--.

Column 16, Line 25, replace "profvided" with --provided--.

Signed and Sealed this
Third Day of March, 2015

Michelle K. Lee
*Deputy Director of the United States Patent and Trademark Office*

SEQUENCE LISTING

```
<160> NUMBER OF SEQ ID NOS: 9

<210> SEQ ID NO 1
<211> LENGTH: 9
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 1 ggcgcgcca                                                                9

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 2
ggccggccgc ggccgcaa                                                     18

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 3 acgcgtatg                                                                9

<210> SEQ ID NO 4
```

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
aacaccaacg gcgcgccaat ggcttccaag gtgtac                          36

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
tgggcataag cagtgatggg agccatacgc gtatcg                          36

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
atagcgctat ggcttccaag gtgtacga                                   28

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
aatgcggccg ctcagaagaa ctcgtca                                    27

<210> SEQ ID NO 8
<211> LENGTH: 9579
<212> TYPE: DNA
<213> ORGANISM: Artificial Sequence
<220> FEATURE:
<223> OTHER INFORMATION: Description of Artificial Sequence: Synthetic construct polynucleotide

<400> SEQUENCE: 8
acctgctctc tatgagagca acactccacc atgaaccgct ccnctgtgag gaactactgt      60
cttcacgcag aaagcgtcta gccatggcgt tagtatgagt gttgtacagc ctccaggacc     120
ccccctcccg ggagagccat agtggtctgc ggaaccggtg agtacaccgg aatcgccggg     180
atgaccgggt cctttcttgg attaacccgc tcaatgcccg gaaatttggg cgtgcccccg     240
caagactgct agccgagtag tgttgggtcg cgaaaggcct tgtggtactg cctgataggg     300
tgcttgcgag tgccccggga ggtctcgtag accgtgcacc atgagcacga atcctaaacc     360
tcaaagaaaa accaaacgta acaccaaccg ccgcccaatg acgttaagt tcccgggtgg     420 tggccagatc gttggcggag tttacttgtt gccgcgcagg ggcccagat tgggtgtgcg     480 cgcgactcgg aagacttcgg agcggtcgca acctcgtgga agacgccaac ctatccccaa     540

```
ggcgcgtcga cccgagggaa ggtcctgggc acaaccagga tatccatggc ctctttacgg    600
taatgagggt tgtgggtggg caggatggct cttgtccccc cgtggctctc gaccgtcttg    660
gggcccaaat gatccccggc ggaggtcccg caatttgggt aaggtcatcg ataccctaac    720
ctgcggcttc gccgacctca tgggatacat cccgctcgta ggcgccccg tgggtggcgt     780 cgccagggcc ctggcacatg gtgtcagggc tttggaggac gggatcaatt atgcaacagg    840
gaatctcccc ggttgctcct tttctatctt cctcttggca cttctttcgt gcctgactgt    900
ccccgcttcg gccgttaact atcgcaatgt ctcgggcatc taccatgtca ccaatgactg    960
cccgaattca agcatagtgt atgaggccga ccatcacatc ttgcaccttc caggttgcgt   1020
gccctgcgtg agagagggga atcagtcacg ctgctgggtg gcccttactc ctaccgtcgc   1080
agcgccatac atcggcgcac cgcttgagtc cttacggagt catgtggatt tgatggtggg   1140
ggccgccact gttttgctcgg gtcttttacat cggggacctg tgtggcggct tgttcctagt  1200
tggccagatg ttttcattcc gaccacggcg ccactggacc acccaggatt gcaattgttc   1260
catctacaca gggcacatta caggccacag aatggcctgg gacatgatga tgaactggag   1320
tccaacaacc accttagttc tcgcccaggt catgaggatc ccaaccactc tggtagactt   1380
actctctgga ggccactggg gtgtcctcgt gggagtggcc tatttcagca tgcaggccaa   1440
ttgggccaaa gtcatcttgg tcctattcct cttttgcaggg gttgatgccg agactcacgt   1500
gtctggggca gcagtcggcc ggagtaccgc cggcttggct aacctctttt cttctgggtc   1560
taagcagaat ttacagctca tcaacagcaa tgggagctgg catataaata ggactgccct   1620
taactgcaat gacagcttaa acactgggtt cttggctagc ttgttctaca cccacaagtt   1680
taacagctca gggtgttccg aacggctcgc gtgctgcaag agccttgaca gctacggcca   1740
aggctggggc ccactcgggg tcgctaacat cagcggctcg tctgatgaca ggccttattg   1800
ctggcactac gcgcctcggc cgtgcgggat tgtgccagca tccagtgtgt gtggccccgt   1860
gtattgtttc actcccagcc ctgtcgtggt cggtactact gatcacgtcg gggtccctac   1920
ttacacctgg ggggagaatg agactgatgt cttccttttg aactcgacca gaccgccgca   1980
tggtgcgtgt tttggatgcg tgtggatgaa cagtaccggg ttcaccaaaa cctgtggcgc   2040
ccctccatgc gaggttaaca ccaataatgg gacctggcac tgccccaccg attgcttcag   2100
gaagcatccg gagactacct acgccaagtg cggatcaggg ccttggatca caccgcgctg   2160
cctgattgat tacccgtacc ggctgtggca tttcccgtgc accgccaact ctccgtcttt   2220
taacatcagg acatttgtcg gcggtataga gcatcggatg caagcggcat gcaactggac   2280
caggggggaa gtctgtggct tggagcacag ggatcgcgta gagctatcac ccctgctcct   2340
taccactaca gcgtggcaga tcctcccctg ctctttcacc actttacctg ccctctccac   2400
cggcttgatc cacctccacc aaaatatcgt ggacgtccag tacctctatg tgttgggtc    2460 tgcagtggta tcttgggccc ttaagtggga atatgtggtg ctcgcgttcc tgcttctcgc   2520
ggacgcgaga gtctctgcct gcctatggat gatgtttatg gtaagtcaag ttgaggcggc   2580
tctgtccaac ctgattaaca tcaatgctgc ttcagccgct ggtgcccaag gcttctggta   2640
cgccatcctc ttcatctgca ttgtctggca tgtcaagggc cggttcccag ctgctgctgc   2700
ctacgcagcc tgcgggctgt ggcccctgtt tctcctgctt ctgatgctgc ctgagagggc   2760
ttatgcatac gaccaggaag tgcagggtc ccttggcggc gccatcgttg tcatgctgac    2820
cattctgaca ctgtctccgc actacaagtt atggctggct agggggattgt ggtggatcca   2880 atattttata gctaggaccg aggctgtgct gcatgtctat attccatcct tcaacgtgcg   2940
```

```
cgggcctcgc gactcagtga ttgttcttgc agtcctggtc tgtccacacc tagtatttga    3000
catcacaaaa tatcttctgg ccatcttagg gcccctccac atactccagg cctcgctcct    3060
acgcatccct tactttgtga gggcacaagc gctggttaag atctgcagct tgttgcgtgg    3120
ggtagtttat ggcaagtact tccaaatggt cgtgcttaaa gcaggggccc tgactggtac    3180
ttacatctat gaccacctta ctcccatgtc agattgggcc gctacgggcc tccgcgattt    3240
ggcggtggcc ctagagccag ttgtgttcac gcccatggaa agaaagtca tcgtctgggg     3300 cgctgacacc gctgcgtgcg gagacatcat aaggggatta cctgtttcgg ccaggttggg    3360
caatgaaatc ttgctcggac cagccgatac agaaacatca aagggtgga gactccttgc     3420 ccccatcaca gcatacgcgc agcagacccg cggcttgttc agcaccatcg taacgagcct    3480
cactggcagg gacaccaatg agaattgtgg cgaagtgcag gtcttatcca ccgctacgca    3540
gtccttcctg ggtactgcgg ttaacggcgt gatgtggacc gtctaccacg gggcgggtgc    3600
caagaccatc agcggcccga agggacctgt caatcaaatg tacactaatg ttgaccaaga    3660
cttggtgggg tggccagcac cccccggagt cagatctctt gctccgtgca cctgcggctc    3720
ggcagacttg tatctagtca ccaggcacgc agatgtaata cccgtgcgca ggagaggaga    3780
caccagagga gctctcttga gccctagacc aatatccact cttaagggat cttccggagg    3840
tccgctgctg tgccccatgg gacacgccgc cggcatattc cgtgcggcgg tgtgtactcg    3900
aggggtagcc aaggcggtag acttcgtccc ggttgaatct cttgagacta ccatgagatc    3960
accagtgttc actgacaact caacacctcc agcagtgccc cagacctacc aggtcgcgca    4020
cctacacgca ccaacaggaa gtggcaagag caccaaagtc ccggcggcgt atgctgccca    4080
aggctataaa gtgctagtgc tcaatccttc ggttgcggcc acactgggtt ttggggtata    4140
catgtccaag gcatatggca tcgacccgaa catccggtcg ggagtcagga ccatcaccac    4200
gggtgcgcca atcacgtact caacgtatgg taagttcctg gctgatggag gttgcagcgg    4260
aggggcatac gacataatca tctgtgacga gtgccattcc actgactcca caacgatcct    4320
tggcataggc acagtcctgg accaagcgga gaccgctgga gtgcgcctca ccgtgctcgc    4380
gactgctact ccgccagggt cagtgactac acctcattcc aacatagagg aggtcgccct    4440
gccaacaacg ggggaaatcc ccttttacgg caaggcgatc cctctggagc tgattaaggg    4500
gggcagacat ctcatcttct gccactcaaa gaaaaagtgt gatgaactgg ccagacaact    4560
gacatctctt ggtctgaatg ccgtagccta ctacagaggc ttagacgttt cggtgattcc    4620
cacgtctggg gacgtcgtgg tatgcgccac ggacgccctc atgacgggtt ttaccggcga    4680
ctttgactca gtgatagact gcaatacatc tgtgatacag actgttgact tcagcttgga    4740
ccccaccttc tccatagaga ctacaaccgt tccccaggac gcggtatccc gcagccagcg    4800
gagaggccgc actggtaggg ggaggttggg cacataccgg tatgtcaccc cgggagagag    4860
accatcaggc atgtttgaca ctgcagtgct ttgcgagtgc tacgatgccg ggtgtgcctg    4920
gtacgagctg acacctgctg aaaccacaac aaggctgaaa gcttacttcg acacaccagg    4980
ccttcctgtg tgccaagacc atctggagtt ctgggagagc gtctttacag gttaacccca    5040
catagacggt catttcctat cccagaccaa gcaatcgggt gagaatttcc cgtatcttgt    5100
tgcttaccaa gccacggtgt gcgccaaggc tctggcgcct ccaccaagct gggacaccat    5160
gtggaagtgc ctaattcgcc ttaagcccac cctgacgggg cccacacccc tcctctacag    5220
actggggtct gtgcagaatg aagtggtgct cacccatccc atcaccaaat acatcatggc    5280
```

```
ttgcatgtca gctgatctcg aggtagtgac aagtacgtgg gtcttggtgg gcggcgtcct    5340
ggcagctctg gctgcttact gtctttcagt gggcagcgta gtgattgttg ggagagtcgt    5400
cctgtcgggc caacctgctg tcattcccga tcgcgaagtg ctctaccaac agttcgacga    5460
aatggaggag tgttccaaac acctcccact agtcgagcac gggttacaac tggctgagca    5520
gttcaagcag aaggccttag gtctcctaaa tttcgctggc aagcaagccc aagaggcaac    5580
accagtgatc cagtctaact tcgctaaact tgagcagttt tgggcgaagc acatgtggaa    5640
tttcatcagc ggcattcaat atctcgctgg actgtctacc ttgccaggca atcctgccat    5700
tgcttccctc atgtccttta ctgctgctgt tacaagccct ctgaccaccc aacaaaccct    5760
cctttttaac atcttggggg gatgggtggc ctcgcagatt gcgactccga cggcttctac    5820
cgcattcgtc gtgagcggct tggcgggggc ggcagttggc agtgtgggcc ttggcaaaat    5880
tttggtggac attctcgccg gttacggcgc cggcgtagct ggcgctgtgg ttaccttcaa    5940
gatcatgagc ggcgagatgc cttccacaga ggacttggta aatttgctcc cggccattct    6000
atcgcccgga gcattggtag tggggtggt atgcgcggcg attttgcgcc gccacgtggg    6060
cccgggcgaa ggggctgtgc agtggatgaa ccgtctaatt gcgttcgcat cgcgaggcaa    6120
tcacgtgtct cccacgcatt acgtccctga gtccgacgcg gcagcccgcg tgaccaccat    6180
actatcatcc ctcactgtga catccctcct cagacgcctc cacaagtgga tcaatgaaga    6240
ttgctccacc ccatgtgccg aatcttggct atggaggta tgggattggg tctgcaccgt    6300
gctgagtgac ttcaagacgt ggctaaaagc caagttgctg cccctcatgc caggcatccc    6360
cttcctctca tgccagaggg gctataaggg agagtggcgc ggagatggcg tgatgcatac    6420
cacatgcccc tgcggagcag atctggcagg tcacatcaag aacggctcga tgagaatcac    6480
cgggccgaaa acctgcagca acacatggca tggtaccttc cccatcaatg cttacaccac    6540
aggccctggt gtacccatcc cggcgccgaa ctacaagttc gcgctttgga gggtgtccgc    6600
cgaggactac gtggaggttc gcagagtggg tgatttccat tatgtcaccg ggtaacaca    6660 agacaacatc aagtgcccct gccaagttcc ggccccagag ttcttcacgg aagtggacgg    6720
catcaggcta caccgccacg ccccgaagtg caaacccttg ctgcgggacg aagtgtcgtt    6780
ctcagtagga ctcaattcgt tcgtagtggg atcacaactc ccatgcgagc cagagccgga    6840
cgtggcagtg ctaacatcca tgctgacaga cccatcacac ataacggcgg aatcggcgcg    6900
tcggagattg gctcgagggt cacgaccctc gctagctagt tcctcggcga gtcagctttc    6960
cgccccgtct ctcaaggcca cgtgtaccgc tccccatgac tcccctggta ctgatctcct    7020
cgaggctaac ctcttgtggg ggtctaccgc taccagggtt gagacggacg agaaggtaat    7080
aatactagac tcttttgagt catgtgtggc tgagccaaat gatgacaggg aagtctcggt    7140
tgccgcggaa atcctgcgtc cgaccaagaa gttccctcca gcactaccga tctgggcccg    7200
gccggattac aatccacctc ttaccgagac gtggaagcag caggactaca agcctccgac    7260
cgtccacggg tgcgctctgc ctcccggcaa gcagcccccc gttcctcctc ccaggaggaa    7320
acggacggta cagctcactg agtccgttgt ttctaccgct ttggcagagc tggccgcaaa    7380 gaccctttggc cagtcagagc cgagctcaga ccgtgataca gaccttacca ccccaactga    7440
gaccacagac tcgggcccca tcgtcgtgga tgatgcatcc gatgacggat cttattcgtc    7500
aatgcctcca ctagagggg agcccggtga cccggacttg acatcagact cttggtccac    7560
tgttagcgga tcgaggacg tcgtgtgctg ctcaatgtca tattcatgga ctggggcgct    7620
tgtaacacct tgcgcggctg aagaatcaaa gctgccaatt agccccctga gcaattcact    7680
```

```
tttgcgccat cacaatatgg tgtatgccac gaccacccgt tctgctgtga cacggcagaa      7740
gaaggtgacc ttcgaccgcc tgcaggtggt ggacagtcac tacaatgaag tgcttaagga      7800
gataaaggca cgagcatcca gagtgaaggc acgcttgctt accacagagg aagcttgcga      7860
cctgacgccc ccccactcag ccagatcaaa gttcggctac ggggcgaagg atgttcggag      7920
ccattcccgc aaggccatta accacatcag ctccgtgtgg aaggacttgc tggacgacaa      7980
caatacccca ataccaacaa caatcatggc caaaaatgag gtcttcgctg tgaacccagc      8040
gaagggaggt cggaagcctg ctcgcctgat cgtgtatccg gatctcgggg tccgggtttg      8100
cgagaagaga gcgcttcacg acgtcatcaa aaaactgcct gaggccgtga tgggagccgc      8160
ttatggcttc caatactccc cagcgcagcg ggtggaattt cttctgactg cttggaagtc      8220
gaagaagacc ccaatggggt tctcttatga tacccgctgc tttgactcca ctgtaaccga      8280
aaaggacatc agggtcgagg aagaggtcta tcagtgttgt gacctggagc cgaagcccg      8340 caaagtcatc accgccctca cagatagact ctatgtgggc ggcccctatgc acaacagcaa      8400 gggagacctt tgtgggtatc ggagatgtcg cgcaagcggc gtctacacca ccagcttcgg      8460
gaacacgctg acgtgctatc tcaaagccac ggccgccatc agggcggcgg ggctgagaga      8520
ctgcactatg ttggttttgcg gtgatgactt agtcgtcatc gctgagagcg acggcgtaga      8580
ggaggacaac cgagccctcc gagccttcac ggaggctatg acgagatact cggctccccc      8640
aggtgacgcc ccgcagccag catatgacct ggaactaata acatcatgtt catccaacgt      8700
ctcagtcgcg cacgacgtga cgggtaaaaa ggtatattac ctaacccgag accctgaaac      8760
tcccttggcg cgagccgcat gggagacagt ccgacacact ccagtcaatt cctggttggg      8820
aaacatcata gtctacgctc ccacaatatg ggtgcgcatg atattgatga cccacttttt      8880
ctcaatactc cagagccagg aagcccttga gaaagcactc gacttcgata tgtacggagt      8940
cacctactct atcactccgc tggatttacc ggcaatcatt caaagactcc atggcttaag      9000
cgcgttcacg ctgcacggat actctccaca cgaactcaac cgggtggccg gagccctcag      9060
aaaacttggg gtaccccgc tgagagcgtg gagacatcgg gcccgagcag tccgcgctaa      9120
gcttatcgcc cagggaggta gagccaaaat atgtggcata tacctcttta actgggcggt      9180
aaaaaccaaa ctcaaactca ctccattgcc tgccgctgcc aaactcgatt tatcgggttg      9240
gtttacggta ggcgccggcg ggggagacat ttatcacagc atgtctcatg cccgaccccg      9300
ctatttactc ctgtgcctac tcctacttac agtagggta ggcatcttcc tgctgcctgc      9360
tcggtaggca gcttaacact ccgaccttag ggtccccttg ttttttttt ttttttttt      9420 ttttttttt ttttttttt ttttttcctt tccttctttc ctttcctaat ctttctttct      9480
tggtggctcc atcttagccc tagtcacggc tagctgtgaa aggtccgtga gccgcatgac      9540
tgcagagagt gctgatactg gcctctctgc agatcatgt                            9579
```

<210> SEQ ID NO 9
<211> LENGTH: 3008
<212> TYPE: PRT
<213> ORGANISM: Artificial Sequence
<220> FEATURE:
<223> OTHER INFORMATION: Description of Artificial Sequence: Synthetic
      construct polypeptide

<400> SEQUENCE: 9

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
        195                 200                 205

Asn Ser Ser Ile Val Tyr Glu Ala Asp His His Ile Leu His Leu Pro
    210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
        275                 280                 285

Gln Met Phe Ser Phe Arg Pro Arg Arg His Trp Thr Thr Gln Asp Cys
    290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
        355                 360                 365

Ala Lys Val Ile Leu Val Leu Phe Leu Phe Ala Gly Val Asp Ala Glu
    370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn

-continued

```
            435                 440                 445
Ser Ser Gly Cys Ser Glu Arg Leu Ala Cys Cys Lys Ser Leu Asp Ser
450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
                500                 505                 510

Ser Pro Val Val Val Gly Thr Thr Asp His Val Gly Val Pro Thr Tyr
                515                 520                 525

Thr Trp Gly Glu Asn Glu Thr Asp Val Phe Leu Leu Asn Ser Thr Arg
530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
                580                 585                 590

Thr Tyr Ala Lys Cys Gly Ser Gly Pro Trp Ile Thr Pro Arg Cys Leu
                595                 600                 605

Ile Asp Tyr Pro Tyr Arg Leu Trp His Phe Pro Cys Thr Ala Asn Phe
610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Leu Thr Thr Thr Ala Trp
                660                 665                 670

Gln Ile Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
                690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
                725                 730                 735

Met Met Phe Met Val Ser Gln Val Glu Ala Ala Leu Ser Asn Leu Ile
                740                 745                 750

Asn Ile Asn Ala Ala Ser Ala Ala Gly Ala Gln Gly Phe Trp Tyr Ala
                755                 760                 765

Ile Leu Phe Ile Cys Ile Val His Val Lys Gly Arg Phe Pro Ala
                770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
                805                 810                 815

Ser Leu Gly Gly Ala Ile Val Val Met Leu Thr Ile Leu Thr Leu Ser
                820                 825                 830

Pro His Tyr Lys Leu Trp Leu Ala Arg Gly Leu Trp Trp Ile Gln Tyr
                835                 840                 845

Phe Ile Ala Arg Thr Glu Ala Val Leu His Val Tyr Ile Pro Ser Phe
850                 855                 860
```

-continued

```
Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
                885                 890                 895

Gly Pro Leu His Ile Leu Gln Ala Ser Leu Leu Arg Ile Pro Tyr Phe
            900                 905                 910

Val Arg Ala Gln Ala Leu Val Lys Ile Cys Ser Leu Leu Arg Gly Val
        915                 920                 925

Val Tyr Gly Lys Tyr Phe Gln Met Val Val Leu Lys Ala Gly Ala Leu
    930                 935                 940

Thr Gly Thr Tyr Ile Tyr Asp His Leu Thr Pro Met Ser Asp Trp Ala
945                 950                 955                 960

Ala Thr Gly Leu Arg Asp Leu Ala Val Ala Leu Glu Pro Val Val Phe
                965                 970                 975

Thr Pro Met Glu Lys Lys Val Ile Val Trp Gly Ala Asp Thr Ala Ala
            980                 985                 990

Cys Gly Asp Ile Ile Arg Gly Leu  Pro Val Ser Ala Arg  Leu Gly Asn
        995                 1000                1005

Glu Ile Leu Leu Gly Pro Ala  Asp Thr Glu Thr Ser  Lys Gly Trp
    1010                1015                1020

Arg Leu Leu Ala Pro Ile Thr  Ala Tyr Ala Gln Gln  Thr Arg Gly
    1025                1030                1035

Leu Phe Ser Thr Ile Val Thr  Ser Leu Thr Gly Arg  Asp Thr Asn
    1040                1045                1050

Glu Asn Cys Gly Glu Val Gln  Val Leu Ser Thr Ala  Thr Gln Ser
    1055                1060                1065

Phe Leu Gly Thr Ala Val Asn  Gly Val Met Trp Thr  Val Tyr His
    1070                1075                1080

Gly Ala Gly Ala Lys Thr Ile  Ser Gly Pro Lys Gly  Pro Val Asn
    1085                1090                1095

Gln Met Tyr Thr Asn Val Asp  Gln Asp Leu Val Gly  Trp Pro Ala
    1100                1105                1110

Pro Pro Gly Val Arg Ser Leu  Ala Pro Cys Thr Cys  Gly Ser Ala
    1115                1120                1125

Asp Leu Tyr Leu Val Thr Arg  His Ala Asp Val Ile  Pro Val Arg
    1130                1135                1140

Arg Arg Gly Asp Thr Arg Gly  Ala Leu Leu Ser Pro  Arg Pro Ile
    1145                1150                1155

Ser Thr Leu Lys Gly Ser Ser  Gly Gly Pro Leu Leu  Cys Pro Met
    1160                1165                1170

Gly His Ala Ala Gly Ile Phe  Arg Ala Ala Val Cys  Thr Arg Gly
    1175                1180                1185

Val Ala Lys Ala Val Asp Phe  Val Pro Val Glu Ser  Leu Glu Thr
    1190                1195                1200

Thr Met Arg Ser Pro Val Phe  Thr Asp Asn Ser Thr  Pro Pro Ala
    1205                1210                1215

Val Pro Gln Thr Tyr Gln Val  Ala His Leu His Ala  Pro Thr Gly
    1220                1225                1230

Ser Gly Lys Ser Thr Lys Val  Pro Ala Ala Tyr Ala  Ala Gln Gly
    1235                1240                1245

Tyr Lys Val Leu Val Leu Asn  Pro Ser Val Ala Ala  Thr Leu Gly
    1250                1255                1260
```

```
Phe Gly Val Tyr Met Ser Lys Ala Tyr Gly Ile Asp Pro Asn Ile
1265                 1270                1275

Arg Ser Gly Val Arg Thr Ile Thr Thr Gly Ala Pro Ile Thr Tyr
1280                 1285                1290

Ser Thr Tyr Gly Lys Phe Leu Ala Asp Gly Gly Cys Ser Gly Gly
1295                 1300                1305

Ala Tyr Asp Ile Ile Ile Cys Asp Glu Cys His Ser Thr Asp Ser
1310                 1315                1320

Thr Thr Ile Leu Gly Ile Gly Thr Val Leu Asp Gln Ala Glu Thr
1325                 1330                1335

Ala Gly Val Arg Leu Thr Val Leu Ala Thr Ala Thr Pro Pro Gly
1340                 1345                1350

Ser Val Thr Thr Pro His Ser Asn Ile Glu Glu Val Ala Leu Pro
1355                 1360                1365

Thr Thr Gly Glu Ile Pro Phe Tyr Gly Lys Ala Ile Pro Leu Glu
1370                 1375                1380

Leu Ile Lys Gly Gly Arg His Leu Ile Phe Cys His Ser Lys Lys
1385                 1390                1395

Lys Cys Asp Glu Leu Ala Arg Gln Leu Thr Ser Leu Gly Leu Asn
1400                 1405                1410

Ala Val Ala Tyr Tyr Arg Gly Leu Asp Val Ser Val Ile Pro Thr
1415                 1420                1425

Ser Gly Asp Val Val Val Cys Ala Thr Asp Ala Leu Met Thr Gly
1430                 1435                1440

Phe Thr Gly Asp Phe Asp Ser Val Ile Asp Cys Asn Thr Ser Val
1445                 1450                1455

Ile Gln Thr Val Asp Phe Ser Leu Asp Pro Thr Phe Ser Ile Glu
1460                 1465                1470

Thr Thr Thr Val Pro Gln Asp Ala Val Ser Arg Ser Gln Arg Arg
1475                 1480                1485

Gly Arg Thr Gly Arg Gly Arg Leu Gly Thr Tyr Arg Tyr Val Thr
1490                 1495                1500

Pro Gly Glu Arg Pro Ser Gly Met Phe Asp Thr Ala Val Leu Cys
1505                 1510                1515

Glu Cys Tyr Asp Ala Gly Cys Ala Trp Tyr Glu Leu Thr Pro Ala
1520                 1525                1530

Glu Thr Thr Thr Arg Leu Lys Ala Tyr Phe Asp Thr Pro Gly Leu
1535                 1540                1545

Pro Val Cys Gln Asp His Leu Glu Phe Trp Glu Ser Val Phe Thr
1550                 1555                1560

Gly Leu Thr His Ile Asp Gly His Phe Leu Ser Gln Thr Lys Gln
1565                 1570                1575

Ser Gly Glu Asn Phe Pro Tyr Leu Val Ala Tyr Gln Ala Thr Val
1580                 1585                1590

Cys Ala Lys Ala Leu Ala Pro Pro Pro Ser Trp Asp Thr Met Trp
1595                 1600                1605

Lys Cys Leu Ile Arg Leu Lys Pro Thr Leu His Gly Pro Thr Pro
1610                 1615                1620

Leu Leu Tyr Arg Leu Gly Ser Val Gln Asn Glu Val Val Leu Thr
1625                 1630                1635

His Pro Ile Thr Lys Tyr Ile Met Ala Cys Met Ser Ala Asp Leu
1640                 1645                1650

Glu Val Val Thr Ser Thr Trp Val Leu Val Gly Gly Val Leu Ala
```

-continued

```
            1655                1660                1665

Ala Leu Ala Ala Tyr Cys Leu Ser Val Gly Ser Val Val Ile Val
    1670                1675                1680

Gly Arg Val Val Leu Ser Gly Gln Pro Ala Val Ile Pro Asp Arg
    1685                1690                1695

Glu Val Leu Tyr Gln Gln Phe Asp Glu Met Glu Glu Cys Ser Lys
    1700                1705                1710

His Leu Pro Leu Val Glu His Gly Leu Gln Leu Ala Glu Gln Phe
    1715                1720                1725

Lys Gln Lys Ala Leu Gly Leu Leu Asn Phe Ala Gly Lys Gln Ala
    1730                1735                1740

Gln Glu Ala Thr Pro Val Ile Gln Ser Asn Phe Ala Lys Leu Glu
    1745                1750                1755

Gln Phe Trp Ala Lys His Met Trp Asn Phe Ile Ser Gly Ile Gln
    1760                1765                1770

Tyr Leu Ala Gly Leu Ser Thr Leu Pro Gly Asn Pro Ala Ile Ala
    1775                1780                1785

Ser Leu Met Ser Phe Thr Ala Ala Val Thr Ser Pro Leu Thr Thr
    1790                1795                1800

Gln Gln Thr Leu Leu Phe Asn Ile Leu Gly Gly Trp Val Ala Ser
    1805                1810                1815

Gln Ile Ala Thr Pro Thr Ala Ser Thr Ala Phe Val Val Ser Gly
    1820                1825                1830

Leu Ala Gly Ala Ala Val Gly Ser Val Gly Leu Gly Lys Ile Leu
    1835                1840                1845

Val Asp Ile Leu Ala Gly Tyr Gly Ala Gly Val Ala Gly Ala Val
    1850                1855                1860

Val Thr Phe Lys Ile Met Ser Gly Glu Met Pro Ser Thr Glu Asp
    1865                1870                1875

Leu Val Asn Leu Leu Pro Ala Ile Leu Ser Pro Gly Ala Leu Val
    1880                1885                1890

Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Thr Ile Leu Ser Ser Leu Thr Val
    1940                1945                1950

Thr Ser Leu Leu Arg Arg Leu His Lys Trp Ile Asn Glu Asp Cys
    1955                1960                1965

Ser Thr Pro Cys Ala Glu Ser Trp Leu Trp Glu Val Trp Asp Trp
    1970                1975                1980

Val Cys Thr Val Leu Ser Asp Phe Lys Thr Trp Leu Lys Ala Lys
    1985                1990                1995

Leu Leu Pro Leu Met Pro Gly Ile Pro Phe Leu Ser Cys Gln Arg
    2000                2005                2010

Gly Tyr Lys Gly Glu Trp Arg Gly Asp Gly Val Met His Thr Thr
    2015                2020                2025

Cys Pro Cys Gly Ala Asp Leu Ala Gly His Ile Lys Asn Gly Ser
    2030                2035                2040

Met Arg Ile Thr Gly Pro Lys Thr Cys Ser Asn Thr Trp His Gly
    2045                2050                2055
```

-continued

```
Thr Phe Pro Ile Asn Ala Tyr Thr Thr Gly Pro Gly Val Pro Ile
    2060            2065            2070
Pro Ala Pro Asn Tyr Lys Phe Ala Leu Trp Arg Val Ser Ala Glu
    2075            2080            2085
Asp Tyr Val Glu Val Arg Arg Val Gly Asp Phe His Tyr Val Thr
    2090            2095            2100
Gly Val Thr Gln Asp Asn Ile Lys Cys Pro Cys Gln Val Pro Ala
    2105            2110            2115
Pro Glu Phe Phe Thr Glu Val Asp Gly Ile Arg Leu His Arg His
    2120            2125            2130
Ala Pro Lys Cys Lys Pro Leu Leu Arg Asp Glu Val Ser Phe Ser
    2135            2140            2145
Val Gly Leu Asn Ser Phe Val Val Gly Ser Gln Leu Pro Cys Glu
    2150            2155            2160
Pro Glu Pro Asp Val Ala Val Leu Thr Ser Met Leu Thr Asp Pro
    2165            2170            2175
Ser His Ile Thr Ala Glu Ser Ala Arg Arg Arg Leu Ala Arg Gly
    2180            2185            2190
Ser Arg Pro Ser Leu Ala Ser Ser Ser Ala Ser Gln Leu Ser Ala
    2195            2200            2205
Pro Ser Leu Lys Ala Thr Cys Thr Ala Pro His Asp Ser Pro Gly
    2210            2215            2220
Thr Asp Leu Leu Glu Ala Asn Leu Leu Trp Gly Ser Thr Ala Thr
    2225            2230            2235
Arg Val Glu Thr Asp Glu Lys Val Ile Ile Leu Asp Ser Phe Glu
    2240            2245            2250
Ser Cys Val Ala Glu Pro Asn Asp Asp Arg Glu Val Ser Val Ala
    2255            2260            2265
Ala Glu Ile Leu Arg Pro Thr Lys Lys Phe Pro Pro Ala Leu Pro
    2270            2275            2280
Ile Trp Ala Arg Pro Asp Tyr Asn Pro Pro Leu Thr Glu Thr Trp
    2285            2290            2295
Lys Gln Gln Asp Tyr Lys Pro Pro Thr Val His Gly Cys Ala Leu
    2300            2305            2310
Pro Pro Gly Lys Gln Pro Pro Val Pro Pro Arg Arg Lys Arg
    2315            2320            2325
Thr Val Gln Leu Thr Glu Ser Val Val Ser Thr Ala Leu Ala Glu
    2330            2335            2340
Leu Ala Ala Lys Thr Phe Gly Gln Ser Glu Pro Ser Ser Asp Arg
    2345            2350            2355
Asp Thr Asp Leu Thr Thr Pro Thr Glu Thr Thr Asp Ser Gly Pro
    2360            2365            2370
Ile Val Val Asp Asp Ala Ser Asp Asp Gly Ser Tyr Ser Ser Met
    2375            2380            2385
Pro Pro Leu Glu Gly Glu Pro Gly Asp Pro Asp Leu Thr Ser Asp
    2390            2395            2400
Ser Trp Ser Thr Val Ser Gly Ser Glu Asp Val Val Cys Cys Ser
    2405            2410            2415
Met Ser Tyr Ser Trp Thr Gly Ala Leu Val Thr Pro Cys Ala Ala
    2420            2425            2430
Glu Glu Ser Lys Leu Pro Ile Ser Pro Leu Ser Asn Ser Leu Leu
    2435            2440            2445
```

```
Arg His His Asn Met Val Tyr Ala Thr Thr Arg Ser Ala Val
2450                2455                2460

Thr Arg Gln Lys Lys Val Thr Phe Asp Arg Leu Gln Val Val Asp
2465                2470                2475

Ser His Tyr Asn Glu Val Leu Lys Glu Ile Lys Ala Arg Ala Ser
2480                2485                2490

Arg Val Lys Ala Arg Leu Leu Thr Thr Glu Glu Ala Cys Asp Leu
2495                2500                2505

Thr Pro Pro His Ser Ala Arg Ser Lys Phe Gly Tyr Gly Ala Lys
2510                2515                2520

Asp Val Arg Ser His Ser Arg Lys Ala Ile Asn His Ile Ser Ser
2525                2530                2535

Val Trp Lys Asp Leu Leu Asp Asp Asn Thr Pro Ile Pro Thr
2540                2545                2550

Thr Ile Met Ala Lys Asn Glu Val Phe Ala Val Asn Pro Ala Lys
2555                2560                2565

Gly Gly Arg Lys Pro Ala Arg Leu Ile Val Tyr Pro Asp Leu Gly
2570                2575                2580

Val Arg Val Cys Glu Lys Arg Ala Leu His Asp Val Ile Lys Lys
2585                2590                2595

Leu Pro Glu Ala Val Met Gly Ala Ala Tyr Gly Phe Gln Tyr Ser
2600                2605                2610

Pro Ala Gln Arg Val Glu Phe Leu Leu Thr Ala Trp Lys Ser Lys
2615                2620                2625

Lys Thr Pro Met Gly Phe Ser Tyr Asp Thr Arg Cys Phe Asp Ser
2630                2635                2640

Thr Val Thr Glu Lys Asp Ile Arg Val Glu Glu Val Tyr Gln
2645                2650                2655

Cys Cys Asp Leu Glu Pro Glu Ala Arg Lys Val Ile Thr Ala Leu
2660                2665                2670

Thr Asp Arg Leu Tyr Val Gly Gly Pro Met His Asn Ser Lys Gly
2675                2680                2685

Asp Leu Cys Gly Tyr Arg Arg Cys Arg Ala Ser Gly Val Tyr Thr
2690                2695                2700

Thr Ser Phe Gly Asn Thr Leu Thr Cys Tyr Leu Lys Ala Thr Ala
2705                2710                2715

Ala Ile Arg Ala Ala Gly Leu Arg Asp Cys Thr Met Leu Val Cys
2720                2725                2730

Gly Asp Asp Leu Val Val Ile Ala Glu Ser Asp Gly Val Glu Glu
2735                2740                2745

Asp Asn Arg Ala Leu Arg Ala Phe Thr Glu Ala Met Thr Arg Tyr
2750                2755                2760

Ser Ala Pro Pro Gly Asp Ala Pro Gln Pro Ala Tyr Asp Leu Glu
2765                2770                2775

Leu Ile Thr Ser Cys Ser Ser Asn Val Ser Val Ala His Asp Val
2780                2785                2790

Thr Gly Lys Lys Val Tyr Tyr Leu Thr Arg Asp Pro Glu Thr Pro
2795                2800                2805

Leu Ala Arg Ala Ala Trp Glu Thr Val Arg His Thr Pro Val Asn
2810                2815                2820

Ser Trp Leu Gly Asn Ile Ile Val Tyr Ala Pro Thr Ile Trp Val
2825                2830                2835

Arg Met Ile Leu Met Thr His Phe Phe Ser Ile Leu Gln Ser Gln
```

-continued

```
              2840           2845                 2850
Glu Ala Leu Glu Lys Ala Leu Asp Phe Asp Met Tyr Gly Val Thr
              2855          2860                 2865
Tyr Ser Ile Thr Pro Leu Asp Leu Pro Ala Ile Ile Gln Arg Leu
              2870          2875                 2880
His Gly Leu Ser Ala Phe Thr Leu His Gly Tyr Ser Pro His Glu
              2885          2890                 2895
Leu Asn Arg Val Ala Gly Ala Leu Arg Lys Leu Gly Val Pro Pro
              2900          2905                 2910
Leu Arg Ala Trp Arg His Arg Ala Arg Ala Val Arg Ala Lys Leu
              2915          2920                 2925
Ile Ala Gln Gly Gly Arg Ala Lys Ile Cys Gly Ile Tyr Leu Phe
              2930          2935                 2940
Asn Trp Ala Val Lys Thr Lys Leu Lys Leu Thr Pro Leu Pro Ala
              2945          2950                 2955
Ala Ala Lys Leu Asp Leu Ser Gly Trp Phe Thr Val Gly Ala Gly
              2960          2965                 2970
Gly Gly Asp Ile Tyr His Ser Met Ser His Ala Arg Pro Arg Tyr
              2975          2980                 2985
Leu Leu Leu Cys Leu Leu Leu Leu Thr Val Gly Val Gly Ile Phe
              2990          2995                 3000
Leu Leu Pro Ala Arg
     3005
```